United States Patent
Han et al.

(10) Patent No.: US 8,927,760 B2
(45) Date of Patent: Jan. 6, 2015

(54) COLCHICINE DERIVATIVES OR PHARMACEUTICALLY ACCEPTABLE SALTS THEREOF, METHOD FOR PREPARING SAID DERIVATIVES, AND PHARMACEUTICAL COMPOSITION COMPRISING SAID DERIVATIVES

(75) Inventors: Duck Jong Han, Seoul (KR); Sung-eun Yoo, Chungcheongnam-do (KR); Jeehee Suh, Daejeon (KR)

(73) Assignee: The Asan Foundation, Seoul (KR)

( * ) Notice: Subject to any disclaimer, the term of this patent is extended or adjusted under 35 U.S.C. 154(b) by 0 days.

(21) Appl. No.: 13/579,704

(22) PCT Filed: Feb. 18, 2011

(86) PCT No.: PCT/KR2011/001087
§ 371 (c)(1),
(2), (4) Date: Sep. 4, 2012

(87) PCT Pub. No.: WO2011/102668
PCT Pub. Date: Aug. 25, 2011

(65) Prior Publication Data
US 2013/0011417 A1  Jan. 10, 2013

(30) Foreign Application Priority Data

Feb. 18, 2010  (KR) ................. 10-2010-0014811

(51) Int. Cl.
C07C 321/00 (2006.01)
C07C 235/56 (2006.01)
C07C 233/32 (2006.01)
A61K 45/06 (2006.01)
C07C 271/24 (2006.01)
A61K 31/165 (2006.01)

(52) U.S. Cl.
CPC ........... *C07C 271/24* (2013.01); *C07C 2101/14* (2013.01); *C07C 2102/08* (2013.01); *C07C 235/56* (2013.01); *C07C 233/32* (2013.01); *C07C 2103/18* (2013.01); *C07C 2102/10* (2013.01); *C07C 2103/34* (2013.01); *C07C 2101/08* (2013.01); *A61K 45/06* (2013.01); *A61K 31/165* (2013.01)
USPC .......................................................... 560/15

(58) Field of Classification Search
USPC ........ 564/123, 182, 180, 52; 560/28, 24, 182; 424/184; 514/480, 595, 617, 613
See application file for complete search history.

(56) References Cited

FOREIGN PATENT DOCUMENTS

| KR | 10-2000-0016387 | 3/2000 |
| KR | 10-2001-0054079 | 7/2001 |
| KR | 10-2002-0030296 | 4/2002 |
| WO | WO97/01570 | 1/1997 |
| WO | WO99/40944 | * 8/1999 |

OTHER PUBLICATIONS

Buddha et al. (New Agents for Prostatic Cancer Activated Specifically by Prostatic Acid Phosphatase, Cancer Treatment Reports vol. 61, No. 2, Mar./Apr. 1977).*
Arnold et al. (Synthesis and characterization of BODIPY-labeled colchicine, Bioorganic & Medicinal Chemistry Letters 18, pp. 5867-5870, 2008).*
Drugs.com (Colchicine (Systemic) Revised Jan. 31, 1994, downloaded from internet Sep. 23, 2013).*
Vogt et al. (Biowaiver Monographs for Immediate Release Solid Oral Dosage Forms: Prednisone, Journal of Pharmaceutical Sciences, vol. 96, No. 6, pp. 1480-1489, 2007).*
Cutler (2007, downloaded from internet on Sep. 24, 2013).*
Ostermann et al. (Colchicine Allows Prolonged Survival of Highly Reactive Renal Allograft in the Rat, Journal of the American society of Nephrology, vol. 4, No. 6, 1993).*
Kerekes et al. ( Synthesis and Biological Effects of Novel Thiocolchicines. 3. Evaluation of N-Acyldeacetylthiocolchicines, N-(Alkoxycarbonyl) deacetylthiocolchicines, and O-Ethyldemethylthiocolchicines. New Synthesis of Thiodemecolcine and Antileukemic Effects of 2-Demethyl- and 3-Demethylthiocolchicine, J. Med. Chem., vol. 28, pp. 1204-1208,1985.*

* cited by examiner

*Primary Examiner* — Brandon Fetterolf
*Assistant Examiner* — Blaine G Doletski
(74) *Attorney, Agent, or Firm* — Cesari and McKenna, LLP

(57) ABSTRACT

The present invention relates to colchicine derivatives expressed in chemical formula 1, or to pharmaceutically acceptable salts thereof, to a method for preparing said derivatives, and to a pharmaceutical composition comprising said derivatives. The colchicine derivatives according to the present invention exhibit superior immunomodulatory effects as compared with conventional immunomodulators or colchicines, and therefore can be valuably used as an immunomodulator for modulating an acute or chronic immune response in organ transplantation.

7 Claims, 2 Drawing Sheets

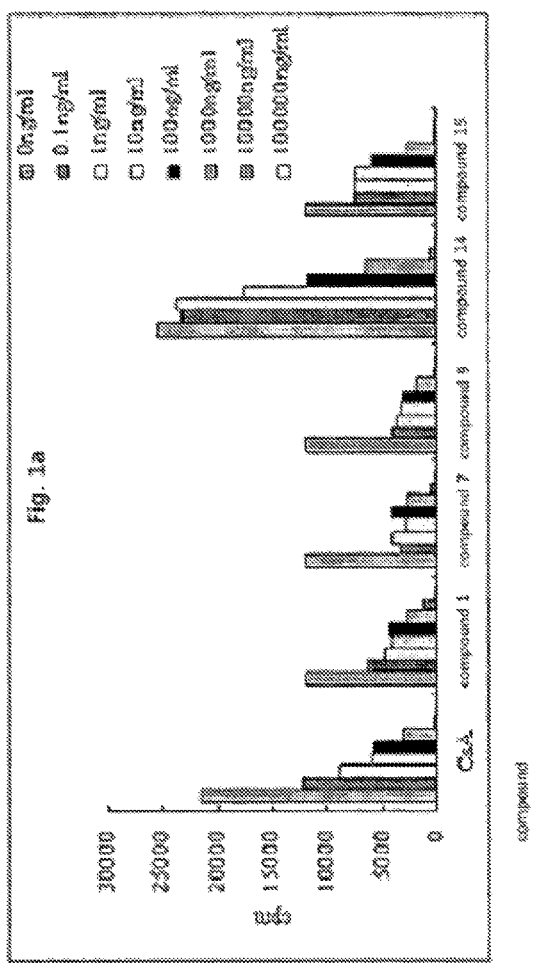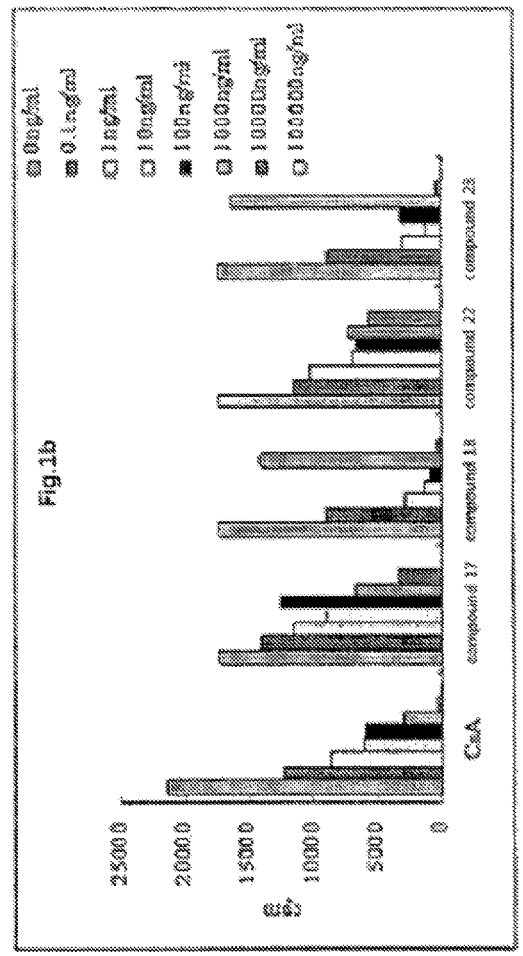

US 8,927,760 B2

COLCHICINE DERIVATIVES OR PHARMACEUTICALLY ACCEPTABLE SALTS THEREOF, METHOD FOR PREPARING SAID DERIVATIVES, AND PHARMACEUTICAL COMPOSITION COMPRISING SAID DERIVATIVES

CROSS REFERENCE TO RELATED APPLICATIONS

This application is a National Stage of International Application No. PCT/KR2011/001087, filed on Feb. 8, 2011, which claims priority to Korean Application No. 10-2010-0014811 filed Feb. 18, 2010. The content of the prior applications is incorporated herein by reference in its entirety.

TECHNICAL FIELD

The present invention relates to colchicine derivatives or pharmaceutically acceptable salts thereof, a method for preparing the same, and a pharmaceutical composition comprising the same. More particularly, the present invention relates to colchicine derivatives which can be used as an immunomodulator of an acute or a chronic immune response in organ transplant.

BACKGROUND ART

Organ transplant rejections, autoimmune diseases, allergies, etc. are caused when the immune system responsible for defending the body activates the defense system against antigens other than the body itself to destroy the transplanted organ or tissue and thus have deleterious effects on the human body. In general, the organ transplant is the most effective treatment for patients with end-stage organ failure. However, if major histocompatibility (MHC) genes of donor and recipient do not match, the body's immune system recognizes the transplanted organ as harmful germs and attacks the transplanted organ by activating T lymphocytes, B lymphocytes, macrophages, or natural killer (NK) cells, etc. The regulation of the unwanted immune response is called immunomodulation, and drugs used for immunomodulation are called immunomodulators. Cyclosporin A, tacrolimus (hereinafter referred to as FK506), etc. have been developed so far as the immunomodulators.

Cyclosporin A was isolated from *Trichoderma polysporum* in 1976 and has been reported to have relatively fewer side effects and to reduce bacterial infection compared to other immunomodulators. Moreover, FK506 isolated from *Streptomyces tsukubaensis* has been reported to have efficiency 10 to 100 times higher than that of cyclosporin A. However, the cyclosporin A and FK506 have side effects such as severe renal toxicity, liver toxicity, etc.

Meanwhile, colchicine is an alkaloid drug used for treatment of gout and has been reported to inhibit the function of tubulin, a protein known to act as both muscle and skeleton, by binding to the tubulin. Colchicine has been reported to have anticancer and antiproliferative activities and has been widely used for treatment of psoriasis or rheumatoid arthritis, treatment of amyloidosis and inflammation, etc. Moreover, Korean Patent No. 324302 and Korean Patent Publication No. 2002-30296 disclose the use of colchicine as an immunomodulator. However, the colchicine has a low effect compared to dose and is highly toxic at high dose, and thus the development of a new improved immunomodulator is urgently needed.

Accordingly, the present inventors have prepared new colchicine derivatives through various synthetic routes and confirmed that the colchicine derivatives exhibit superior immunomodulatory effects and low toxicity compared to conventional immunomodulators and colchicines, thus completing the present invention.

DISCLOSURE

Technical Problem

An object of the present invention is to provide colchicine derivatives or pharmaceutically acceptable salts thereof.

Another object of the present invention is to provide a method for preparing the colchicine derivatives.

Still another object of the present invention is to provide a pharmaceutical composition for immunomodulation comprising the colchicine derivatives or the pharmaceutically acceptable salts thereof as an active ingredient.

Technical Solution

In one aspect, the present invention provides a colchicine derivative or a pharmaceutically acceptable salt thereof represented by the following formula 1:

[Formula 1]

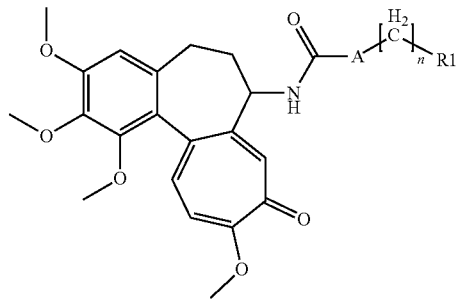

wherein R1 is phenyl,

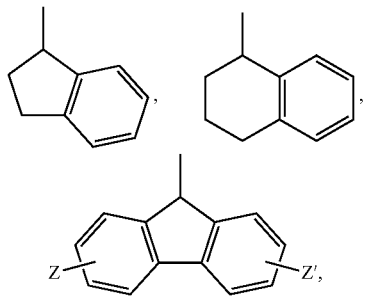

or $C_3$-$C_6$ cycloalkyl, unsubstituted or substituted with X, where X is halogen, $OCH_3$, $NO_2$, $NH_2$ or $C_1$-$C_3$ straight or branched chain alkyl, and Z and Z' are each independently H, halogen, $OCH_3$, $NO_2$, $NH_2$ or $C_1$-$C_4$ straight or branched chain alkyl;

n is an integer from 0 to 3; and

A is $CH_2$, NH, or O.

In another aspect, the present invention provides a method for preparing a colchicine derivative of the following formula 1, the method comprising the step of reacting a deacetyl colchicine derivative represented by the following formula 2 with an equivalent amount or an excess of

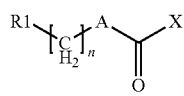

in the presence of a base or a condensing agent in a reaction solvent to form amide.

[Formula 1]

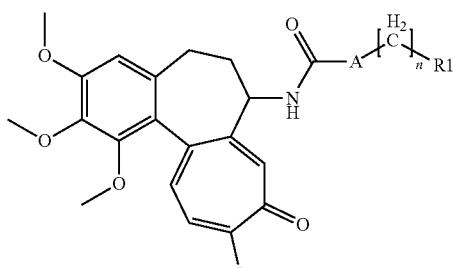

[Formula 2]

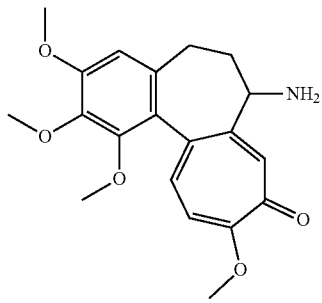

wherein R1, n, and A have the meanings as defined above.

In still another aspect, the present invention provides a pharmaceutical composition for immunomodulation comprising the colchicine derivative or the pharmaceutically acceptable salts thereof as an active ingredient.

Advantageous Effects

The colchicine derivatives or the pharmaceutically acceptable salts thereof of the present invention have no cytotoxicity at high dose and exhibit superior immunomodulatory effects compared to conventional immunomodulators or colchicines, and thus can be effectively used as an immunomodulator for modulating an acute or chronic immune response in organ transplantation.

DESCRIPTION OF DRAWINGS

FIG. 1a and FIG. 1b are graphs showing the modulation or immunomodulatory effects of T-cell proliferation using spleens of Lewis rats and Wistar rats treated with colchicine derivatives (compounds 1, 7, 9, 14, 15, 17, 18, 22, and 23) of the present invention to examine the immunomodulatory effects of the colchicine derivatives.

BEST MODE FOR CARRYING OUT THE INVENTION

Figure 2:
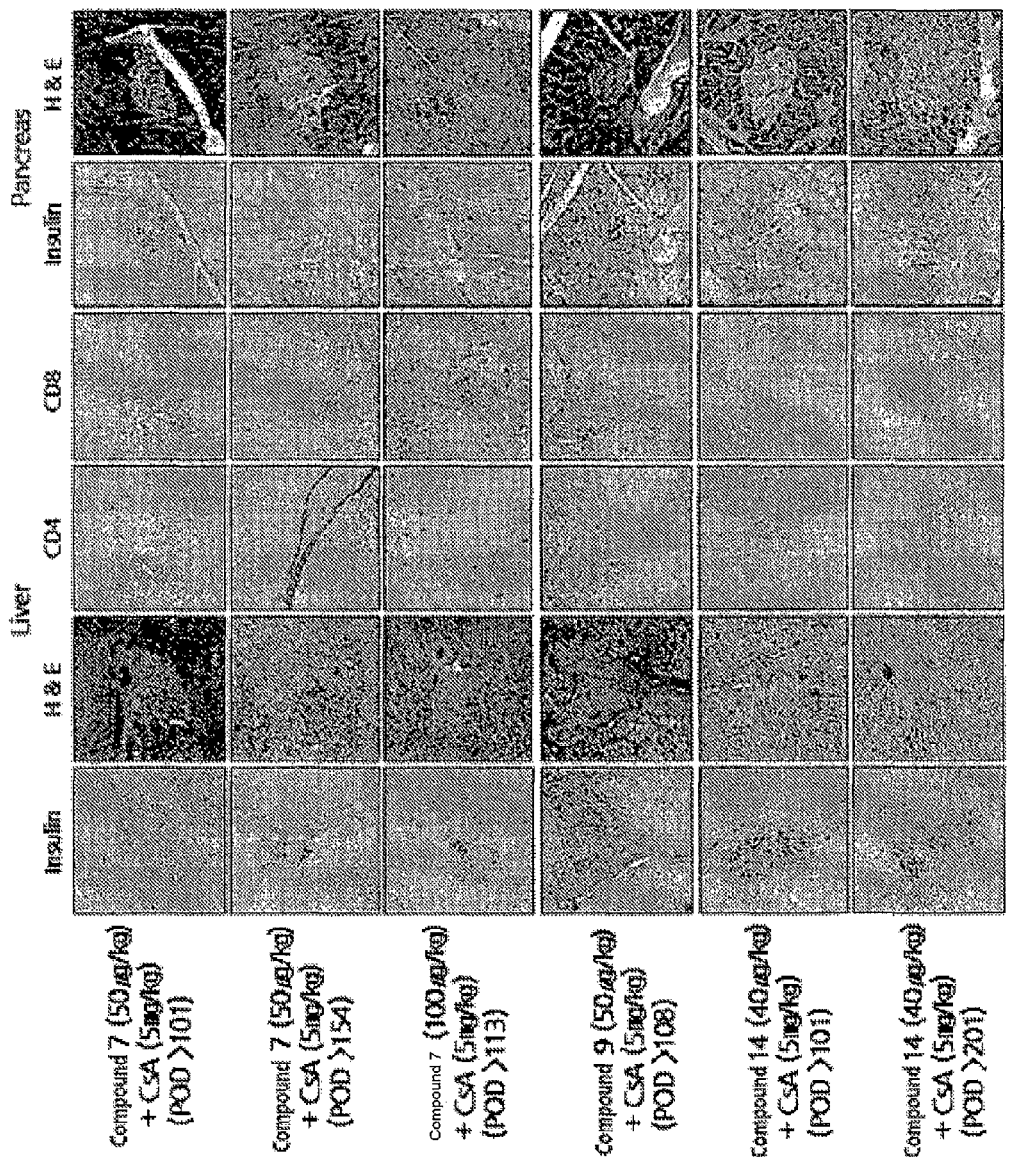
FIG. 2 shows the results of tissue analysis performed 100 days after islet cell transplant by intraperitoneal injection in combination with cyclosporin A (5 mg/kg) and colchicine derivative compounds 7 (50, 100 μg/kg), 9 (50 μg/kg), and 14 (40 μg/kg), in which liver tissues were stained with insulin, hematoxylin and eosin (H&E), and CD4 and CD8, and pancreatic tissues were stained with insulin and H&E. POD is an acronym for "post-operative day."

Hereinafter, the present invention will be described in more detail.

The present invention provides a colchicine derivative or a pharmaceutically acceptable salt thereof represented by the following formula 1:

[Formula 1]

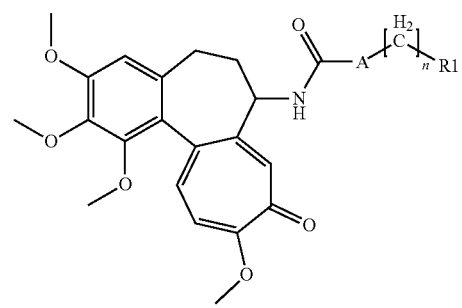

wherein R1 is phenyl,

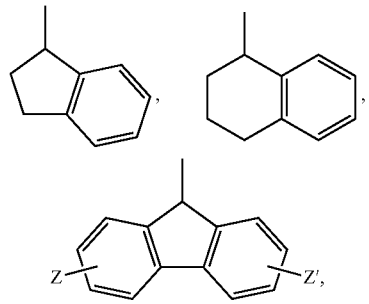

or $C_3$-$C_6$ cycloalkyl, unsubstituted or substituted with X, where X is halogen, $OCH_3$, $NO_2$, $NH_2$ or $C_1$-$C_3$ straight or branched chain alkyl, and Z and Z' are each independently H, halogen, $OCH_3$, $NO_2$, $NH_2$ or $C_1$-$C_4$ straight or branched chain alkyl; n is an integer from 0 to 3; and A is $CH_2$, NH, or O.

Preferably, the colchicine derivative or the pharmaceutically acceptable salt thereof according the present invention may be a compound represented by the above formula 1 wherein R1 is phenyl,

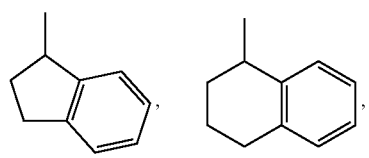

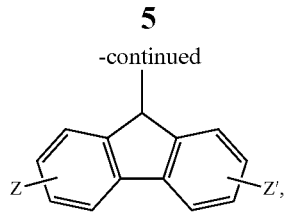

or $C_5$-$C_6$ cycloalkyl, unsubstituted or substituted with X, where X is halogen, $OCH_3$, $NO_2$, or $C_1$-$C_3$ straight or branched chain alkyl, and Z and Z' are each independently H, halogen, or $C_1$-$C_4$ straight or branched chain alkyl; n is an integer from 0 to 2; and A is $CH_2$, NH, or O.

More preferably, the colchicine derivative or the pharmaceutically acceptable salt thereof according the present invention may be a compound represented by the above formula 1 wherein R1 is phenyl,

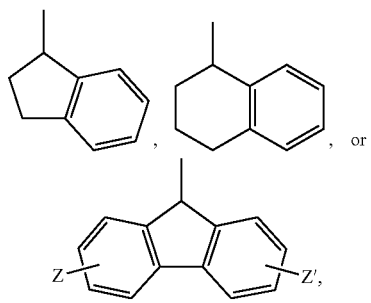

unsubstituted or substituted with X, where X is halogen, $OCH_3$, $NO_2$, or $C_1$-$C_3$ straight or branched chain alkyl, and Z and Z' are each independently H, halogen, or $C_1$-$C_4$ straight or branched chain alkyl; n is an integer from 0 to 2; and A is $CH_2$ or O.

Most preferably, the colchicine derivatives according to present invention may comprise:

1) (1,2,3,10-tetramethoxy-9-oxo-5,6,7,9-tetrahydro-benzo[a]heptalen-7-yl)-carbamic acid benzyl ester;
2) (1,2,3,10-tetramethoxy-9-oxo-5,6,7,9-tetrahydro-benzo[a]heptalen-7-yl)-carbamic acid 4-nitro benzyl ester;
3) (1,2,3,10-tetramethoxy-9-oxo-5,6,7,9-tetrahydro-benzo[a]heptalen-7-yl)-carbamic acid 4-bromo benzyl ester;
4) (1,2,3,10-tetramethoxy-9-oxo-5,6,7,9-tetrahydro-benzo[a]heptalen-7-yl)-carbamic acid 4-fluoro benzyl ester;
5) (1,2,3,10-tetramethoxy-9-oxo-5,6,7,9-tetrahydro-benzo[a]heptalen-7-yl)-carbamic acid 2-fluoro benzyl ester;
6) (1,2,3,10-tetramethoxy-9-oxo-5,6,7,9-tetrahydro-benzo[a]heptalen-7-yl)-carbamic acid 3-fluoro benzyl ester;
7) (1,2,3,10-tetramethoxy-9-oxo-5,6,7,9-tetrahydro-benzo[a]heptalen-7-yl)-carbamic acid 4-methoxy benzyl ester;
8) (1,2,3,10-tetramethoxy-9-oxo-5,6,7,9-tetrahydro-benzo[a]heptalen-7-yl)-carbamic acid 4-methyl benzyl ester;
9) (1,2,3,10-tetramethoxy-9-oxo-5,6,7,9-tetrahydro-benzo[a]heptalen-7-yl)-carbamic acid 4-isopropyl benzyl ester;
10) (1,2,3,10-tetramethoxy-9-oxo-5,6,7,9-tetrahydro-benzo[a]heptalen-7-yl)-carbamic acid cyclopentylmethyl ester;
11) (1,2,3,10-tetramethoxy-9-oxo-5,6,7,9-tetrahydro-benzo[a]heptalen-7-yl)-carbamic acid cyclohexylmethyl ester;
12) (1,2,3,10-tetramethoxy-9-oxo-5,6,7,9-tetrahydro-benzo[a]heptalen-7-yl)-carbamic acid indan-1-ylmethyl ester;
13) (1,2,3,10-tetramethoxy-9-oxo-5,6,7,9-tetrahydro-benzo[a]heptalen-7-yl)-carbamic acid 1,2,3,4-tetrahydro-naphthalen-1-ylmethyl ester;
14) (1,2,3,10-tetramethoxy-9-oxo-5,6,7,9-tetrahydro-benzo[a]heptalen-7-yl)-carbamic acid 9H-fluoren-9-ylmethyl ester;
15) (1,2,3,10-tetramethoxy-9-oxo-5,6,7,9-tetrahydro-benzo[a]heptalen-7-yl)-carbamic acid 1-methyl-9H-fluoren-9-ylmethyl ester;
16) (1,2,3,10-tetramethoxy-9-oxo-5,6,7,9-tetrahydro-benzo[a]heptalen-7-yl)-carbamic acid 2-bromo-9H-fluoren-9-ylmethyl ester;
17) (1,2,3,10-tetramethoxy-9-oxo-5,6,7,9-tetrahydro-benzo[a]heptalen-7-yl)-carbamic acid 2,7-di-tert-butyl-9H-fluoren-9-ylmethyl ester;
18) (1,2,3,10-tetramethoxy-9-oxo-5,6,7,9-tetrahydro-benzo[a]heptalen-7-yl)-carbamic acid 2-(9H-fluoren-9-yl)-ethyl ester;
19) 2-phenyl-N-(1,2,3,10-tetramethoxy-9-oxo-5,6,7,9-tetrahydro-benzo[a]heptalen-7-yl)-acetamide;
20) 2-(4-methoxy-phenyl)-N-(1,2,3,10-tetramethoxy-9-oxo-5,6,7,9-tetrahydro-benzo[a]heptalen-7-yl)-acetamide;
21) 3-phenyl-N-(1,2,3,10-tetramethoxy-9-oxo-5,6,7,9-tetrahydro-benzo[a]heptalen-7-yl)-propionamide;
22) 3-(4-methoxy-phenyl)-N-(1,2,3,10-tetramethoxy-9-oxo-5,6,7,9-tetrahydro-benzo[a]heptalen-7-yl)-propionamide;
23) 2-(9H-fluoren-9-yl)-N-(1,2,3,10-tetramethoxy-9-oxo-5,6,7,9-tetrahydro-benzo[a]heptalen-7-yl)-acetamide;
24) 3-(9H-fluoren-9-yl)-N-(1,2,3,10-tetramethoxy-9-oxo-5,6,7,9-tetrahydro-benzo[a]heptalen-7-yl)-propionamide; and
25) 1-benzyl-3-(1,2,3,10-tetramethoxy-9-oxo-5,6,7,9-tetrahydro-benzo[a]heptalen-7-yl)-urea.

The structures of the above compounds are shown in the following table 1.

TABLE 1

| Compound | Structure |
|---|---|
| 1 | 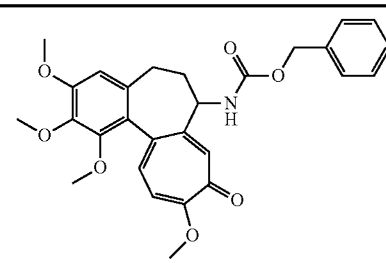 |
| 2 | 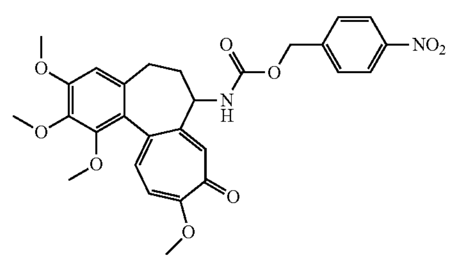 [SMILES: COc1cc2c(c(OC)c1OC)-c1ccc(OC)c(=O)cc1C(NC(=O)OCc1ccc([N+](=O)[O-])cc1)CC2] |
| 3 | 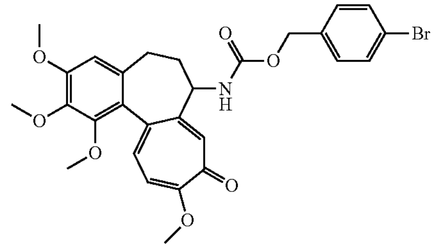 [SMILES: COc1cc2c(c(OC)c1OC)-c1ccc(OC)c(=O)cc1C(NC(=O)OCc1ccc(Br)cc1)CC2] |

TABLE 1-continued
| Compound | Structure |
|---|---|
| 4 | 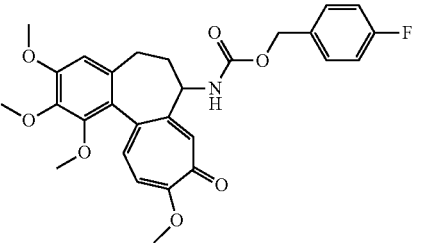 [SMILES: COc1cc2c(c(OC)c1OC)-c1ccc(OC)c(=O)cc1C(NC(=O)OCc1ccc(F)cc1)CC2] |
| 5 | 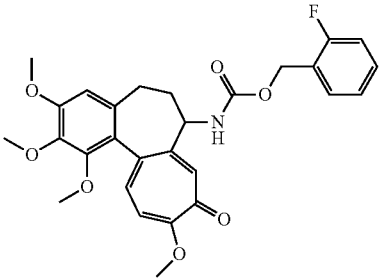 [SMILES: COc1cc2c(c(OC)c1OC)-c1ccc(OC)c(=O)cc1C(NC(=O)OCc1ccccc1F)CC2] |
| 6 | 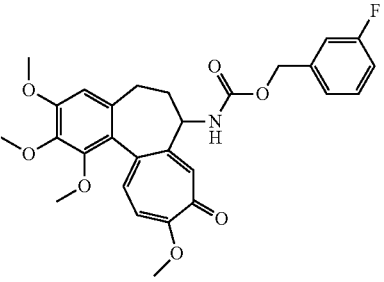 [SMILES: COc1cc2c(c(OC)c1OC)-c1ccc(OC)c(=O)cc1C(NC(=O)OCc1cccc(F)c1)CC2] |
| 7 | 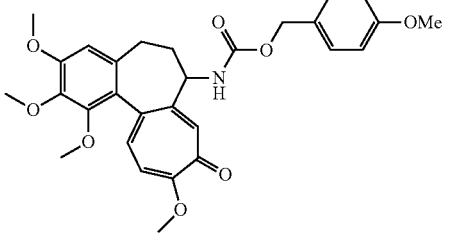 |
| 8 | 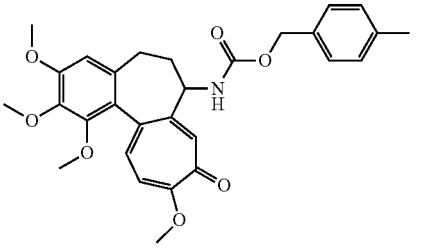 |
| 9 | 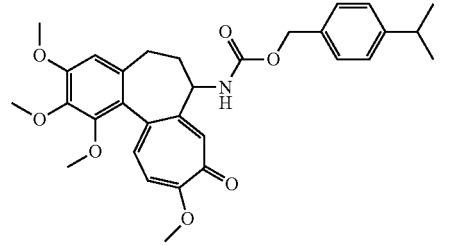 [SMILES: COc1cc2c(c(OC)c1OC)-c1ccc(OC)c(=O)cc1C(NC(=O)OCc1ccc(C(C)C)cc1)CC2] |
| 10 | 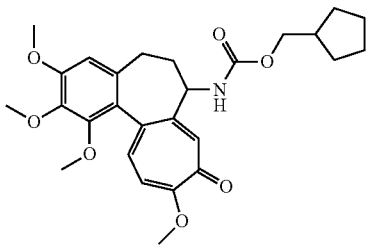 [SMILES: COc1cc2c(c(OC)c1OC)-c1ccc(OC)c(=O)cc1C(NC(=O)OCC1CCCC1)CC2] |
| 11 | 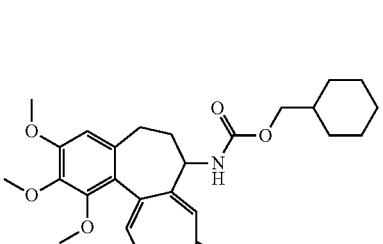 |
| 12 | 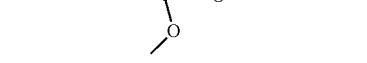 |
| 13 | 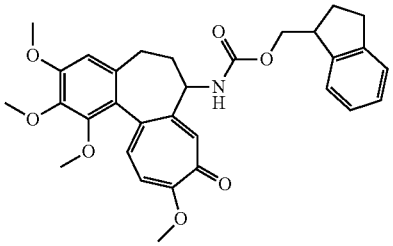 [SMILES: COc1cc2c(c(OC)c1OC)-c1ccc(OC)c(=O)cc1C(NC(=O)OCC1CCc3ccccc31)CC2] |
| 14 | 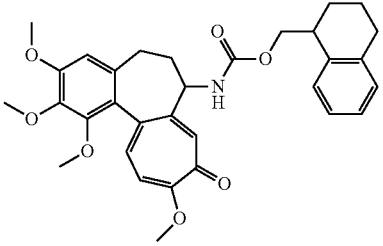 [SMILES: COc1cc2c(c(OC)c1OC)-c1ccc(OC)c(=O)cc1C(NC(=O)OCC1CCCc3ccccc31)CC2] |

TABLE 1-continued
| Compound | Structure |
|---|---|
| 15 | 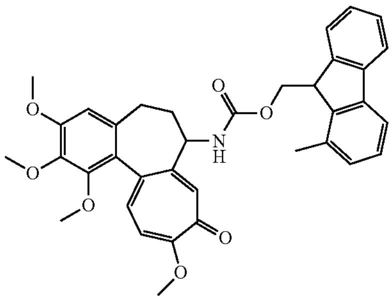 [SMILES: COc1cc2c(c(OC)c1OC)-c1ccc(OC)c(=O)cc1C(NC(=O)OCC1c3ccccc3-c3cccc(C)c31)CC2] |
| 16 | 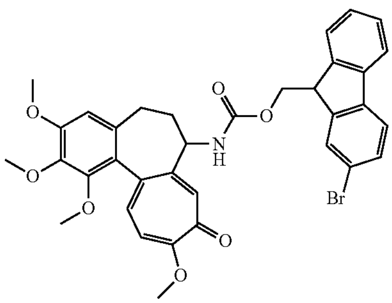 [SMILES: COc1cc2c(c(OC)c1OC)-c1ccc(OC)c(=O)cc1C(NC(=O)OCC1c3ccccc3-c3ccc(Br)cc31)CC2] |
| 17 | 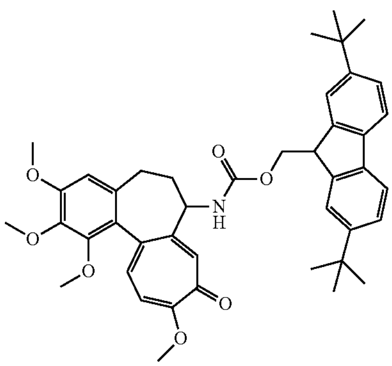 [SMILES: COc1cc2c(c(OC)c1OC)-c1ccc(OC)c(=O)cc1C(NC(=O)OCC1c3cc(C(C)(C)C)ccc3-c3ccc(C(C)(C)C)cc31)CC2] |
| 18 | 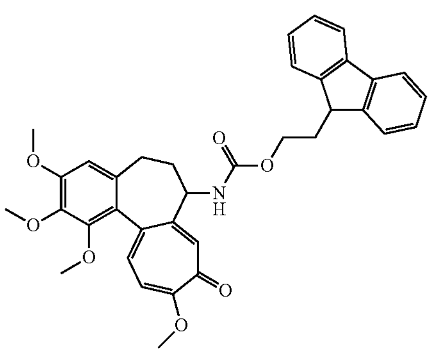 [SMILES: COc1cc2c(c(OC)c1OC)-c1ccc(OC)c(=O)cc1C(NC(=O)OCCC1c3ccccc3-c3ccccc31)CC2] |
| 19 | 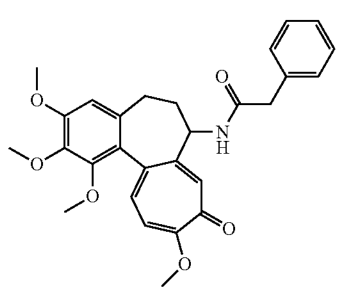 [SMILES: COc1cc2c(c(OC)c1OC)-c1ccc(OC)c(=O)cc1C(NC(=O)Cc1ccccc1)CC2] |
| 20 | |
| 21 | |
| 22 | |
| 23 | |
| 24 | |
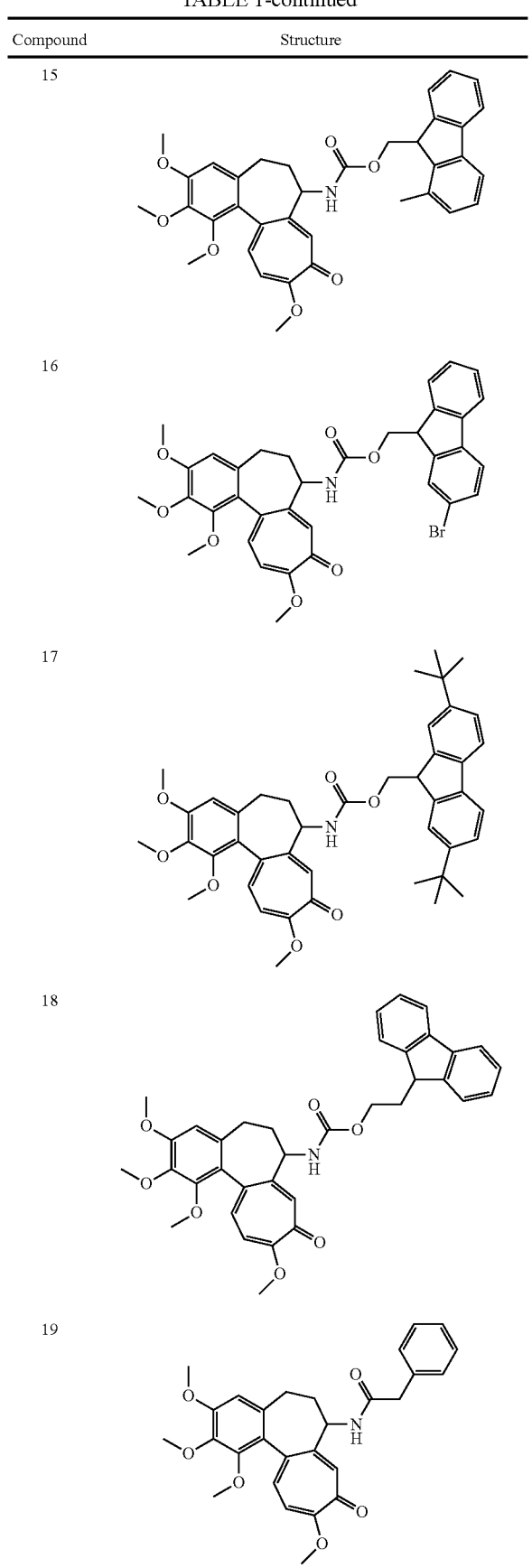
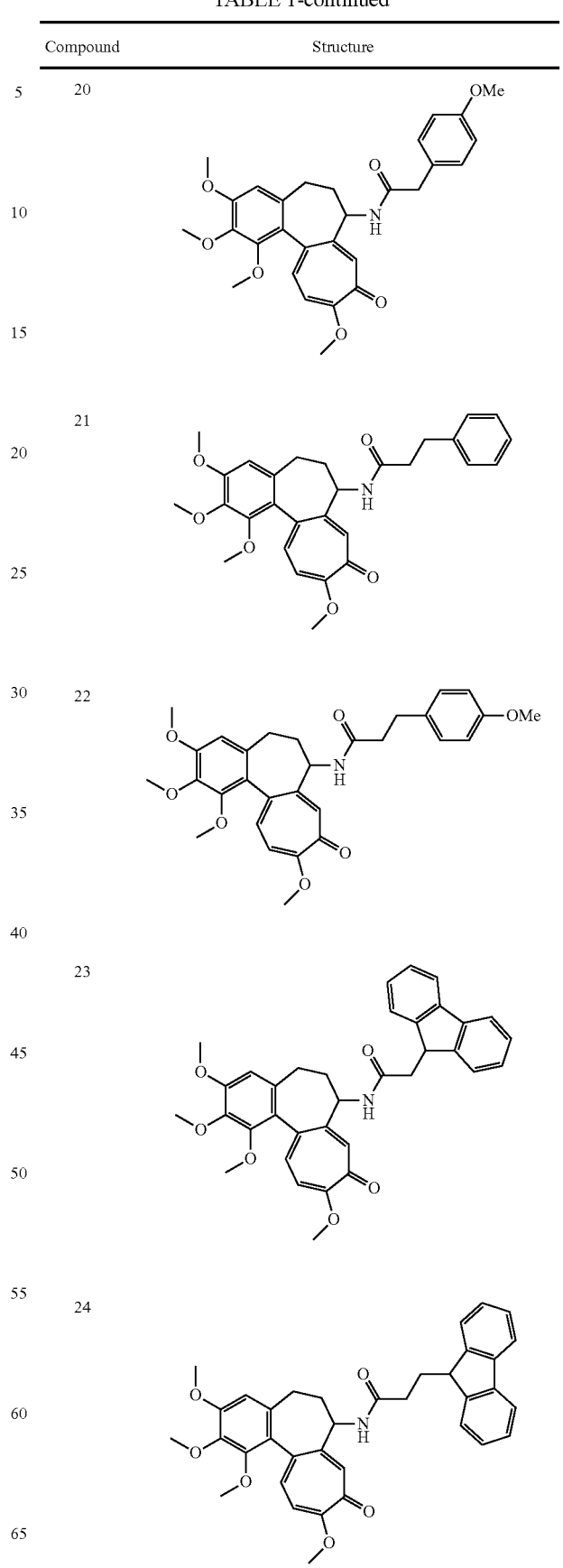

TABLE 1-continued

| Compound | Structure |
|---|---|
| 25 | 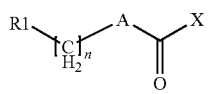 |

Moreover, the present invention provides a method for preparing a colchicine derivative, the method comprising the step of obtaining a colchicine derivative (formula 1-1) by reacting a deacetyl colchicine derivative (formula 2) with an equivalent amount or an excess of in the presence of a base or a condensing agent in a reaction solvent to form amide as shown in the following reaction scheme 1.

[Reaction Scheme 1]

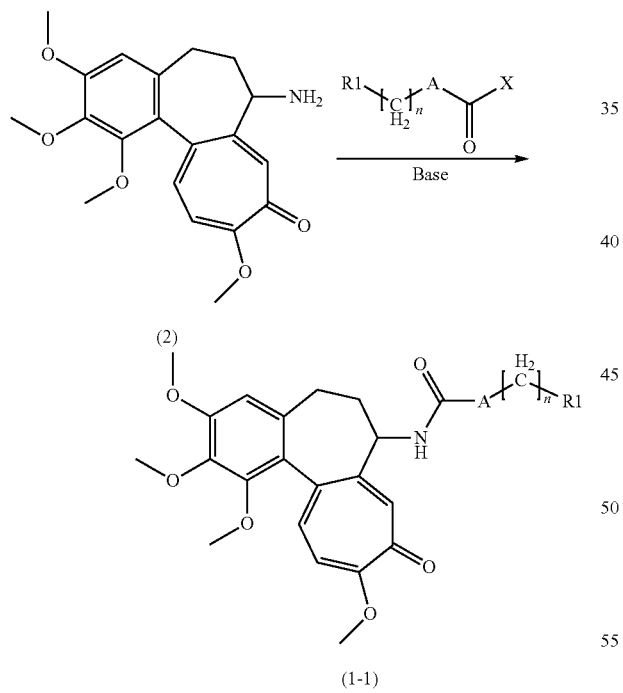

(wherein R1 and n are as defined in formula 1, A is $CH_2$ or O, and X is a hydroxyl group or a chloride group.)

In the preparation method according to the present invention, an organic base such as pyridine, triethylamine, N,N-diisopropylethylamine, DBU, etc. or an inorganic base such as NaOH, $Na_2CO_3$, $K_2CO_3$, $Cs_2CO_3$, etc. may preferably be used as the base. As the condensing agent, 1,3-dicyclohexylcarbodiimide (DCC), N,N'-diisopropylcarbodiimide (DIC), 1-[3-(dimethylamino)propyl]-3-ethylcarbodiimide (EDC), 1,1'-carbonyldiimidazole (CDI), etc. may preferably be used. As the reaction solvent, an ether solvent such as tetrahydrofuran, dioxane, dichloromethane, 1,2-dimethoxyethane, etc., N,N'-dimethyl formamide (DMF), dimethyl sulfoxide, chloroform, or mixtures thereof may preferably used. The reaction temperature may preferably be 0° C. or the boiling point of the solvent.

More preferably, when A is $CH_2$ or O and X is a chloride group, an equivalent amount or an excess of an organic base such as pyridine, triethylamine, N,N'-diisopropyl ethylamine, DBU, etc. or an inorganic base such as NaOH, $Na_2CO_3$, $K_2CO_3$, $Cs_2CO_3$, etc. may preferably be used as the base. As the reaction solvent, an ether solvent such as tetrahydrofuran, dioxane, dichloromethane, 1,2-dimethoxyethane, etc., N,N'-dimethyl formamide (DMF), dimethyl sulfoxide, etc. or mixtures thereof may preferably be used. The reaction may be performed in the temperature range of 0° C. to the boiling point of the solvent. Meanwhile, when A is $CH_2$ and X is a hydroxyl group, DCC, DIC, EDC, CDI, etc. may be used as the condensing agent. As the reaction solvent, dichloromethane, chloroform, tetrahydrofuran, DMF, etc. or mixtures thereof may be used. The reaction may be performed at room temperature to the boiling point of the solvent.

Meanwhile, in the above formula 1, a compound (formula 1-2) in which R1 is phenyl, n is 1, and A is NH may be prepared by reacting a deacetyl colchicine derivative (formula 2) with an equivalent amount or an excess of benzyl isocyanate in a reaction solvent to form urea as shown in the following reaction scheme 2.

[Reaction Scheme 2]

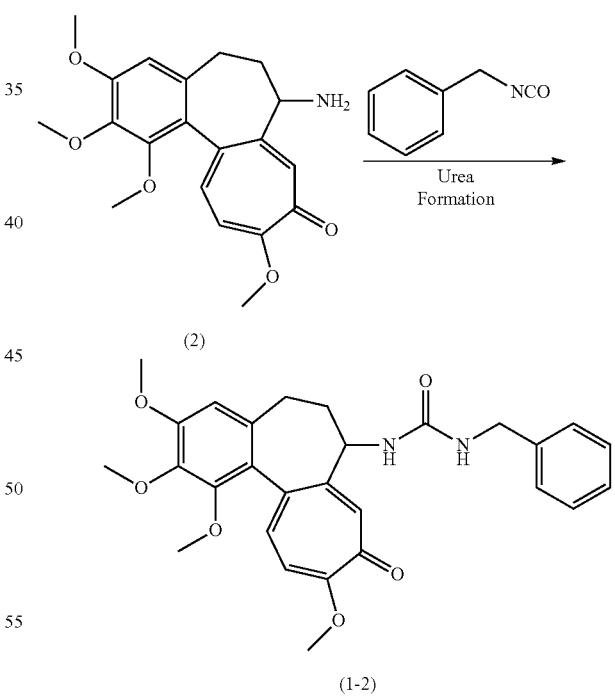

As the reaction solvent, an ether solvent such as tetrahydrofuran, dioxane, dichloromethane, 1,2-dimethoxyethane, etc., dimethylformamide (DMF), dimethylsulfoxide, etc. or mixtures thereof may preferably used. The reaction may be performed in the temperature range of 0° C. to the boiling point of the solvent.

The deacetyl colchicine derivative of formula 2 used as a starting material in reaction schemes 1 and 2 may be prepared from commercially available colchicine by carbamate formation reaction, amide hydrolysis, and amine formation reaction as shown in the following reaction scheme 3 (Helv. Chem. Acta 1996, 79, 2346).

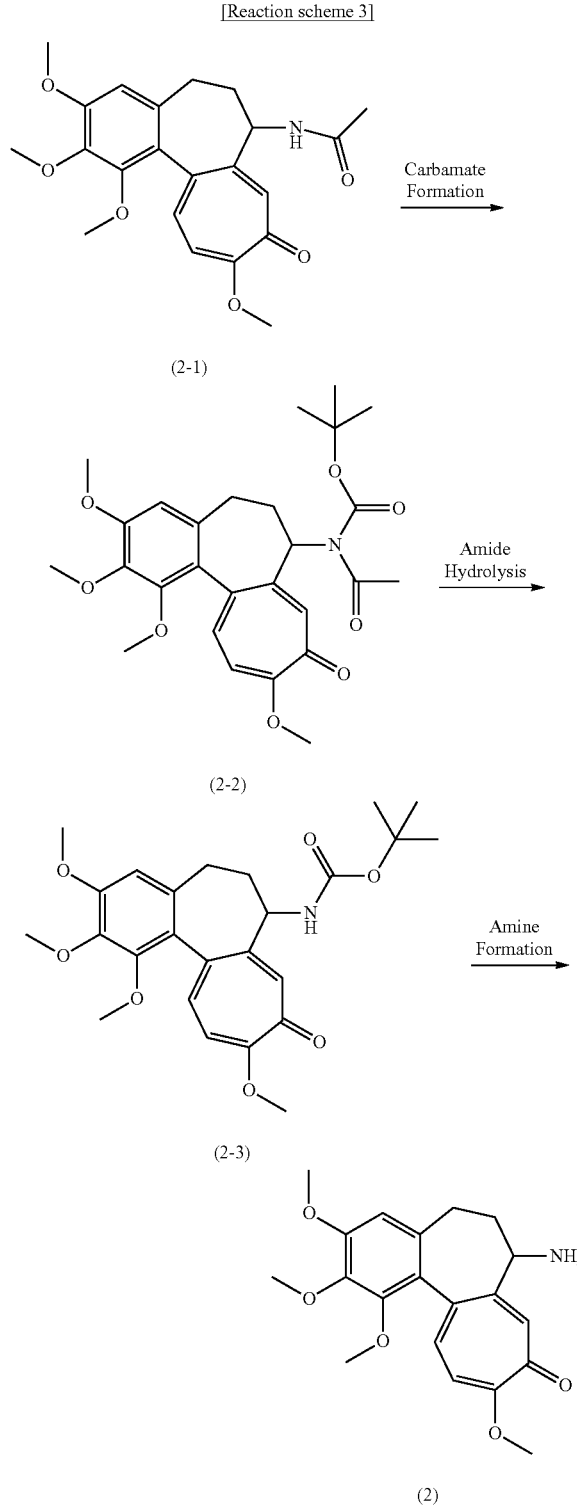

The compound of the following formula 3 reacted with the deacetyl colchicine derivative (formula 2) of reaction scheme 1 may be prepared by the following method.

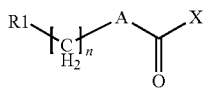

(wherein R1 and n are as defined in formula 1, A is CH$_2$ or O, and X is a hydroxyl group or a chloride group.)

In general, the compound of formula 3 may be prepared by using a commercially available compound or by synthesis according to the following reaction scheme 4. Meanwhile, when R1 is

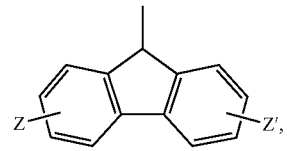

X is a hydroxyl group, A is CH$_2$, and n is 1, the compound of formula 3 may be prepared by synthesis according to the following reaction 5. Here, Z and Z' are each independently H.

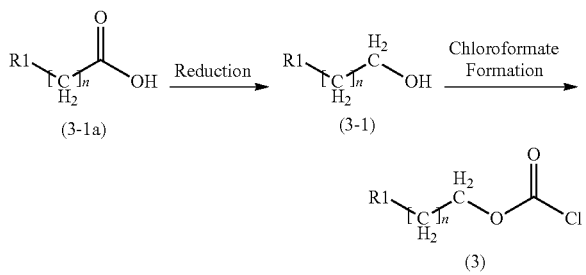

(wherein R1 is

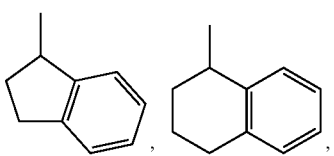

where n is 0, if R1 is

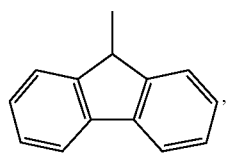

n is 1.)

In the above reaction scheme 4, the carboxylic acid (3-1a) is reduced to an alcohol group with a lithium aluminum hydride or a borane tetrahydrofuran complex using tetrahydrofuran as a reaction solvent, thus preparing an alcohol derivative. The reducing agent may be used in excess, and the reaction temperature may be 0° C. to room temperature. After obtaining chloroformate as an intermediate compound by using an equivalent amount or an excess of phosgene and triphosgene, the alcohol derivative (3-1) obtained in reaction scheme 4 is not purified any further and reacted with compound (2) of reaction scheme 1. Here, as the reaction solvent, dichloromethane, chloroform, tetrahydrofuran, etc. may be used, and the reaction temperature may be 0° C. to room temperature.

[Reaction Scheme 5]

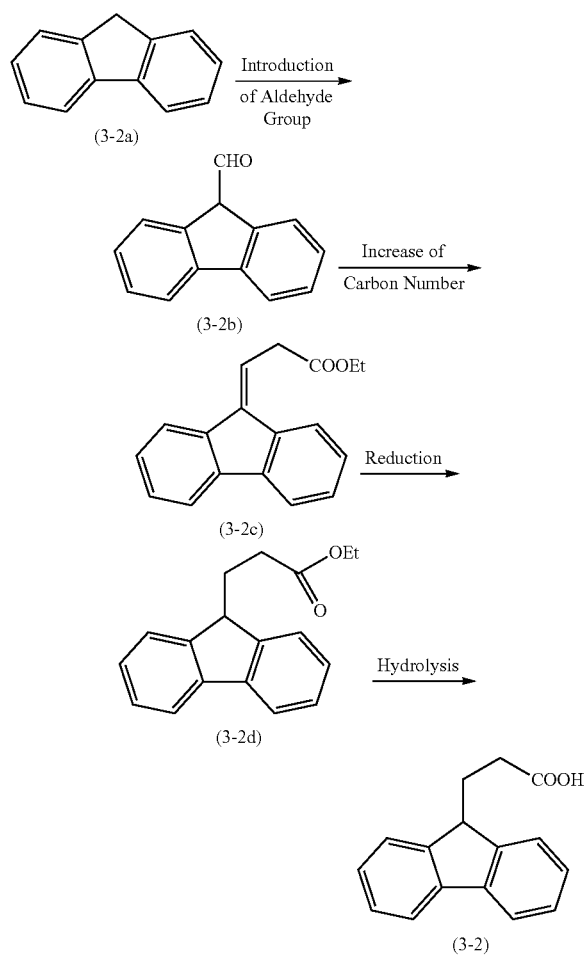

Fluorene (3-2a) used as a starting material in reaction scheme 5 is stirred at 0° C. for 30 minutes using an equivalent amount or an excess of sodium hydride as a base and then reacted with ethyl formate, thus preparing the compound (3-2b) in which an aldehyde group is introduced at C-9. Here, as the reaction solvent, dichloromethane, chloroform, tetrahydrofuran, DMF, etc. may be used. The reaction temperature may be 0° C. to room temperature.

The ester compound (3-2c) in reaction scheme 5 with an exo-double bond at C-9 may be prepared by reacting the aldehyde compound (3-2b) with an equivalent amount or an excess of triphenyl(carbethoxymethylene)phosphorane and an excess of benzoic carboxylic acid. Here, benzene or toluene may be used as the reaction solvent, and the reaction may be performed at room temperature to the boiling point of the solvent.

In the reduction reaction, the compound (3-2d) may be prepared by hydrogenation using hydrogen gas in the presence of a palladium catalyst (Pd/C) or a raney nickel catalyst or by reacting a hydrazine hydride with raney nickel, SnCl$_2$.HCl, Fe.HCl, etc. In general, the reaction is performed in an alcohol solvent such as methanol.

In the above reaction scheme, the carboxylic acid derivative (3-2) may be prepared by hydrolysis of the ester group of the compound (3-2d) with a base. As the solvent, an alcohol solvent such as methanol, an ester solvent such as tetrahydrofuran, dioxane, etc., or mixtures thereof may be used. As the base, sodium hydroxide, potassium hydroxide, etc. may be used. Here, the amount of base used may be 1 to 5 equivalents, and the reaction temperature may be 0° C. or the boiling point of the solvent.

The present invention comprises the colchicine derivatives or the pharmaceutically acceptable salts thereof and further comprises all solvates, hydrates, and stereoisomers, which can be prepared therefrom. Moreover, the pharmaceutically acceptable salts of the colchicine derivatives according to the present invention may be acid addition salts formed by pharmaceutically acceptable free acids. As the free acids, organic acids and inorganic acids may be used. As the inorganic acids, hydrochloric acid, bromic acid, sulfuric acid, sulfurous acid, phosphoric acid, etc. may be used. As the organic acids, citric acid, acetic acid, maleic acid, fumaric acid, gluconic acid, methanesulfonic acid, acetic acid, glycolic acid, succinic acid, tartaric acid, 4-toluenesulfonic acid, galacturonic acid, glutamic acid, aspartic acid, etc. may be used. Preferably, methanesulfonic acid, hydrochloric acid, etc. may be used.

The acid addition salts according to the present invention may be prepared by a typical method of dissolving the compound of formula 1 in a water-miscible organic solvent such as acetone, methanol, ethanol, acetonitrile, etc. adding an excess of an organic acid or an aqueous solution of an inorganic acid, and the precipitating or crystallizing the resulting mixture. Then, the solvent or an excess of the acid may be evaporated from the mixture and then dried to obtain acid addition salts or the precipitated salts may be filtered off and recrystallized.

The present invention provides a pharmaceutical composition for immunomodulation comprising the colchicine derivatives or pharmaceutically acceptable salts thereof as an active ingredient. The immunomodulation may modulate an acute or chronic immune response in organ transplantation.

The colchicine derivatives or the pharmaceutically acceptable salts thereof of the present invention has superior immunomodulatory effects, low side effects, and high survival rates after organ transplant, compared to conventional immunomodulators and colchicines, and thus can be effectively used.

The colchicine derivatives of the present invention may be used alone or in combination with other conventional immunomodulators. The usage may depend on the tissues from which the immunomodulatory effects are achieved. For example, in the case of tissues (e.g., heart), which is vulnerable to the immune response, significant effects can be achieved only with the colchicine derivatives of the present invention. However, in the case of tissues (e.g., islet cells) it is more advantageous to use the colchicine derivatives of the present invention in combination with other conventional immunomodulators (e.g., cyclosporin). Examples of available immunomodulators may include cyclosporin A, tacrolimus, prednisolone, deflazacort, mycophenolic acid, azathioprine, mizoribine, sirolimus, everolimus, anti-CD25 antibody (Simulect and Zenapax), anti-CD3 antibody (OKT3), and anti-CD20 antibody (rituximab).

The colchicine derivative compound of formula 1 according to the present invention may be administered orally or parenterally during clinical administration and may be formulated into various pharmaceutical preparations.

During the formulation of preparations, diluents or excipients such as fillers, extenders, binders, wetting agents, disintegrants, surfactants, etc. may be used. Solid preparations for oral administration may be prepared by mixing at least one compound of the present invention with at least one excipient such as starch, calcium carbonate, sucrose or lactose, gelatin, etc. Moreover, in addition to simple excipients, lubricants such as magnesium stearate or talc may be used. Liquid preparations for oral administration may include suspensions, internal solutions, emulsions, syrups, etc. In addition to simple diluents such as water and liquid paraffin, various excipients such as wetting agents, sweeteners, aromatics, preservatives, etc. may be included. Formulations for parenteral administration may include sterilized aqueous or non-aqueous solutions, suspensions, emulsions, lyophilization preparations, or suppositories. Propylene glycol, polyethylene glycol, vegetable oil such as olive oil, injectable esters such as ethyl oleate, etc. may be used as the non-aqueous solutions or suspensions. Witepsol, macrogol, Tween 61, cocoa butter, laurin butter, glycerol, gelatin, etc. may be used as a base of the suppository.

The effective dose of the compound according to the present invention administered to the body may depend on the age, weight, gender, administration route, health conditions, and seriousness of a patient. For a patient weighing 70 kg, the dose may be 0.1 to 1,000 mg/day, preferably 1 to 500 mg/day, most preferably 0.7 to 3.5 mg/day. Moreover, with the advice of a doctor or pharmacist, the compound according to the present invention may be administered once or several times a day at regular intervals.

Furthermore, the present invention provides a method for inhibiting an immune response in organ transplant, the method comprising administering the colchicine derivatives according to the present invention to a subject requiring the same. In addition, the present invention provides a method for inhibiting an immune response in organ transplant, the method comprising administering the colchicine derivatives according to the present invention in combination with other immunomodulators.

Mode for Invention

Hereinafter, the present invention will be described in more detail with reference to the following Examples. However, the following Examples are only for understanding the configuration and operation of the present invention, but the scope of the present invention is not limited to these Examples.

In the present invention, the molecular structures of the compounds were determined by infrared spectroscopy, NMR spectroscopy, mass spectroscopy, liquid chromatography, X-ray crystallography, optical rotation spectroscopy, elemental analysis, or comparison studies between the calculated values and the experimentally observed values of representative compounds.

PREPARATION EXAMPLE 1

Preparation of 7-amino-1,2,3,10-tetramethoxy-6,7-dihydro-5H-benzo[a]heptalen-9-one (Formula 2) as Starting Material <1-1> Preparation of acetyl-(1,2,3,10-tetramethoxy-9-oxo-5,6,7,9-tetrahydro-benzo[a]heptalen-7-yl)-carbamic acid t-butyl ester (2-2)

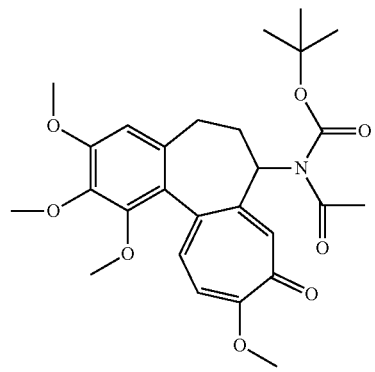 [SMILES: COc1cc2c(c(OC)c1OC)-c1ccc(OC)c(=O)cc1C(N(C(C)=O)C(=O)OC(C)(C)C)CC2]

100 mg (0.25 mmol) of colchicine was dissolved in 5 mL of methylene chloride, and then 104 μl (0.75 mmol, 3 eq) of triethylamine, 546 mg (2.5 mmol, 10 eq) of di-t-butyl dicarbonate, and 546 mg (0.25 mmol, 1 eq) of dimethylaminopyridine were added and stirred at 50° C. for 48 hours. The solvent was removed under reduced pressure, the residue was dissolved again in 50 mL of methylene chloride, and then the organic layer was washed with distilled water three times. The organic layer was dried with anhydrous sodium sulfate and filtered, and the residue obtained by concentrating the filtrate under reduced pressure was purified by silica column chromatography (5% methanol/methylene chloride) to give 75 mg of a yellow foam solid compound (yield: 75%).

$^1$H-NMR (300 MHz, CDCl$_3$) δ 1.56 (s, 9H), 1.92-2.0 (m, 1H), 2.28 (s, 3H), 2.45-2.54 (m, 1H), 2.57-5.71 (m, 2H), 3.66 (s, 3H), 3.90 (s, 3H), 3.93 (s, 3H), 3.97 (s, 3H), 5.11-5.17 (m, 1H), 6.53 (s, 1H), 6.74-6.78 (d, 1H, J=10.5 Hz), 7.18-7.22 (d, 1H, J=10.5 Hz), 7.57 (s, 1H)

MS (m/e, M+): 499

<1-2> Preparation of (1,2,3,10-tetramethoxy-9-oxo-5,6,7,9-tetrahydro-benzo[a]heptalen-7-yl)-carbamic acid t-butyl ester (2-3)

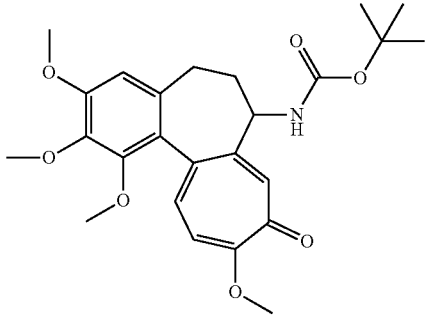 [SMILES: COc1cc2c(c(OC)c1OC)-c1ccc(OC)c(=O)cc1C(NC(=O)OC(C)(C)C)CC2]

100 mg (0.2 mmol) of the compound obtained in the above <1-1> was dissolved in 4 mL of methanol, and then 0.15 mL (0.3 mmol, 1.5 eq) of 2N sodium methoxide was added and stirred at room temperature for 1 hour. The solvent was removed under reduced pressure, the residue was dissolved again in 50 mL of ethyl acetate, and then the organic layer was washed with distilled water three times. The organic layer was dried with anhydrous sodium sulfate and filtered, and the filtrate was concentrated under reduced pressure to give 80 mg of a yellow foam solid compound (yield: 88%).

$^1$H-NMR (300 MHz, CDCl$_3$) δ 1.24 (s, 9H), 1.61-1.69 (m, 1H), 2.15-2.34 (m, 2H), 2.38-2.44 (m, 1H), 3.54 (s, 3H), 3.79 (s, 3H), 3.82 (s, 3H), 3.89 (s, 3H), 4.26-4.34 (m, 1H), 6.44 (s, 1H), 6.71-6.74 (d, 1H, J=10.9 Hz), 7.13-7.17 (d, 1H, J=10.9 Hz), 7.44 (s, 1H)

MS (m/e, M+): 457

<1-3> Preparation of 7-amino-1,2,3,10-tetramethoxy-6,7-dihydro-5H-benzo[a]heptalen-9-one (2)

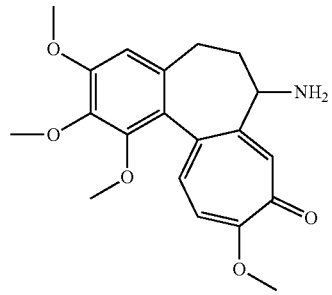 [SMILES: COc1cc2c(c(OC)c1OC)-c1ccc(OC)c(=O)cc1C(N)CC2]

100 mg (0.22 mmol) of the compound obtained in the above <1-2> was dissolved in a 10 mL solution of trifluoroacetic acid and methylene chloride (1:10) and then stirred at room temperature for 24 hours. The solvent was removed under reduced pressure, and the residue was dissolved again in 50 mL of methylene chloride and then added to a saturated aqueous solution of sodium bicarbonate to be basified to pH 9. The organic layer was extracted and washed with distilled water three times. The organic layer was dried with anhydrous sodium sulfate and filtered, and the residue obtained by concentrating the filtrate under reduced pressure was purified by silica column chromatography (10% methanol/methylene chloride) to give 57 mg of a yellow foam solid compound (yield: 76%).

$^1$H-NMR (300 MHz, CDCl$_3$) δ=1.6-1.64 (m, 1H), 2.31-2.47 (m, 3H), 3.66 (s, 3H), 3.69-3.74 (m, 1H), 3.91 (s, 3H), 3.99 (s, 3H), 3.69-3.74 (m, 1H), 3.91 (s, 6H), 3.99 (s, 3H), 6.54 (s, 1H), 6.78-6.82 (d, 1H, J=10.8 Hz), 7.18-7.21 (d, 1H, J=10.8 Hz) 7.74 (s, 1H)

MS (m/e, M+): 357

PREPARATION EXAMPLE 2

Preparation of Compound of Formula 3 as Starting Material

<2-1> Preparation of indan-1-yl-methanol

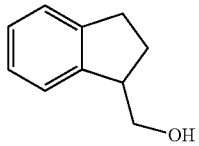 [SMILES: OCC1CCc2ccccc21]

150 mg (0.92 mmol) of indan-1-carboxylic acid compound was dissolved in 9 mL of tetrahydrofuran, and then 105 mg (2.77 mmol) of lithium aluminum hydride was added at 0° C. and stirred at room temperature for 2 hours. Water was slowly added to quench the reaction, and when a gel was formed by adding ethyl acetate, the celite was filtered. Then, the residue was dissolved again in 20 mL of ethyl acetate and the organic layer was washed with distilled water three times. The organic layer was dried with anhydrous sodium sulfate and filtered, and the filtrate was concentrated under reduced pressure to give 124 mg of colorless oil (yield: 91%).

$^1$H-NMR (300 MHz, CDCl$_3$) δ 1.89-2.00 (m, 1H), 2.21-2.33 (m, 1H), 2.83-3.01 (m, 2H), 3.34-3.39 (m, 1H), 3.76-3.82 (m, 2H), 7.15-7.30 (m, 4H)

MS (m/e, M+): 148

<2-2> Preparation of (1,2,3,4-tetrahydro-naphthalen-1-yl)-methanol

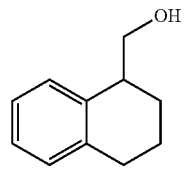 [SMILES: OCC1CCCc2ccccc21]

200 mg (1.10 mmol) of 1,2,3,4-tetrahydro-naphthalen-1-carboxylic acid compound was dissolved in 9 mL of tetrahydrofuran, and then 129 mg (3.30 mmol) of lithium aluminum hydride was added at 0° C. and stirred at room temperature for 1 hour. Water was slowly added to quench the reaction, and when a gel was formed by adding ethyl acetate, the celite was filtered. Then, the residue was dissolved again in 20 mL of ethyl acetate and the organic layer was washed with distilled water three times. The organic layer was dried with anhydrous sodium sulfate and filtered, and the filtrate was concentrated under reduced pressure to give 180 mg of colorless oil (yield: 97%).

$^1$H-NMR (300 MHz, CDCl$_3$) δ 1.69-1.98 (m, 4H), 2.74-2.78 (m, 2H), 2.94-3.01 (m, 1H), 3.80 (d, 2H, J=8.3 Hz), 7.07-7.24 (m, 4H)

MS (m/e, M+): 162

<2-3> Preparation of 2-(9H-fluoren-9-yl)-ethanol

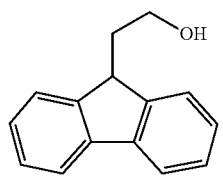 [SMILES: OCCC1c2ccccc2-c2ccccc21]

200 mg (0.89 mmol) of (9H-fluoren-9-yl)acetic acid was dissolved in 9 mL of tetrahydrofuran, and then 101 mg (2.67 mmol) of lithium aluminum hydride was added at 0° C. and stirred at room temperature for 2 hours. Water was slowly added to quench the reaction, and when a gel was formed by adding ethyl acetate, the celite was filtered. Then, the residue was dissolved again in 20 mL of ethyl acetate and the organic layer was washed with distilled water three times. The organic layer was dried with anhydrous sodium sulfate and filtered, and the filtrate was concentrated under reduced pressure. The obtained residue was purified by silica column chromatography (ethyl acetate:hexane=1:3) to give 88 mg of a white solid compound (yield: 47%).

$^1$H NMR (300 MHz, CDCl$_3$) δ 1.16 (br s, 1H), 2.26-2.33 (m, 2H), 3.55-2.63 (m, 2H), 4.10-4.14 (t, 1H), 7.24-7.39 (m, 4H), 7.52-7.54 (d, 1H, J=7.2 Hz), 7.74-7.77 (d, 1H, J=7.2 Hz)

MS (m/e, M+): 210

<2-4> Preparation of 3-fluoren-9-ylidene-propionic acid ethyl ester (3-2c)

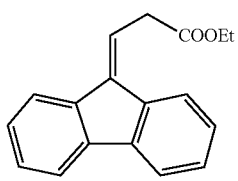 [SMILES: CCOC(=O)CC=C1c2ccccc2-c2ccccc21]

100 mg (0.6 mmol) of fluorene was dissolved in 10 mL of tetrahydrofuran, and then 72 mg (1.8 mmol) of sodium hydride was added at 0° C. and stirred for 1 hour. Then, 0.48 mL (6 mmol) of ethylformate was added and stirred at room temperature for 2 hours. The reactants were dissolved in 50 mL of ethyl acetate, and the organic layer was washed with distilled water three times. The organic layer was dried with anhydrous sodium sulfate and filtered, and the filtrate was concentrated under reduced pressure. The residue was dissolved in 10 mL of benzene, and then 250 mg (0.72 mmol) of triphenyl(carbethoxymethylene)-phosphorane and 73 mg (0.6 mmol) of benzoic acid were added and stirred at 80° C. for 24 hours. The solvent was removed under reduced pressure, the residue was dissolved again in 50 mL of ethyl acetate, and then the organic layer was washed with distilled water three times. The organic layer was dried with anhydrous sodium sulfate and filtered, and the residue obtained by concentrating the filtrate under reduced pressure was purified by silica column chromatography (ethyl acetate:hexane=1:40) to give 80 mg of a white solid compound (yield: 50%).

$^1$H-NMR (300 MHz, CDCl$_3$) δ 1.30-1.34 (t, 3H, J=7.1 Hz), 3.86-3.88 (d, 2H, J=7.1 Hz), 6.93-6.98 (t, 1H, J=6.9 Hz), 7.25-7.40 (m, 4H), 7.67-7.78 (m, 4H)

MS (m/e, M+): 264

<2-5> Preparation of 3-(9H-fluoren-9-yl)-propionic acid ethyl ester (3-2d)

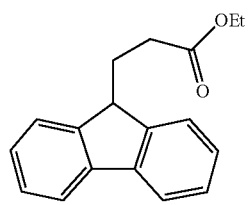 [SMILES: CCOC(=O)CCC1c2ccccc2-c2ccccc21]

160 mg (0.61 mmol) of the compound obtained in the above <2-4> was dissolved in methanol, and then 16 mg of 10% palladium/charcoal was added dropwise, purged with hydrogen gas and stirred at room temperature for 24 hours. After the reaction was quenched, the reaction solution was filtered through celite and evaporated under reduced pressure to give 159 mg of a white solid compound (yield: 98%).

$^1$H-NMR (300 MHz, CDCl$_3$) δ 1.13-1.18 (t, 3H, J=7.1 Hz), 1.92-1.97 (m, 2H), 2.39-2.46 (m, 2H), 3.97-4.04 (m, 2H), 4.05-4.09 (m, 1H), 7.25-7.49 (m, 4H), 7.50-7.52 (d, 2H, J=6.9 Hz), 7.73-7.75 (d, 2H, J=7.4 Hz)

MS (m/e, M+): 266

<2-6> Preparation of 3-(9H-fluoren-9-yl)-propionic acid (3-2)

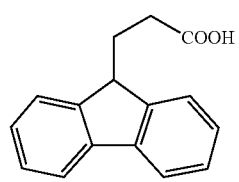 [SMILES: O=C(O)CCC1c2ccccc2-c2ccccc21]

157 mg (0.59 mmol) of the compound obtained in the above <2-5> was dissolved in 10 mL of tetrahydrofuran, and then 0.59 mL (1.18 mmol) of a 2N sodium hydroxide solution was added and stirred at 80° C. for two hours. 2N hydrochloric acid was added to the reactants to be acidified to pH 4 and dissolved in 40 mL (20 mL×2) of ethyl acetate, and then the organic layer was extracted. The organic layer was dried with anhydrous sodium sulfate and filtered, and the filtrate was concentrated under reduced pressure to give 131 mg of a white solid compound (yield: 94%).

$^1$H-NMR (300 MHz, DMSO-d$_6$) δ 1.84-1.91 (m, 2H), 2.22-2.29 (m, 2H), 4.04-4.07 (t, 1H), 7.31-7.41 (m, 4H), 7.58-7.60 (d, 2H, J=7.2 Hz), 7.86-7.89 (d, 2H, J=7.2 Hz)

MS (m/e, M+): 238

EXAMPLE 1

Preparation of (1,2,3,10-tetramethoxy-9-oxo-5,6,7,9-tetrahydro-benzo[a]heptalen-7-yl)-carbamic acid benzyl ester (Compound 1)

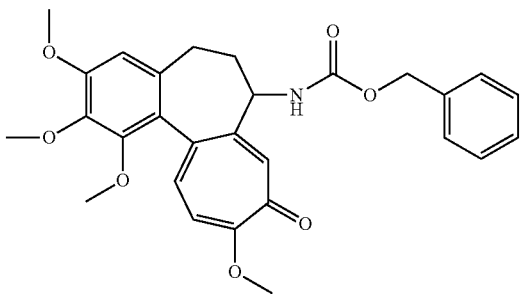 [SMILES: COc1cc2c(c(OC)c1OC)-c1ccc(OC)c(=O)cc1C(NC(=O)OCc1ccccc1)CC2]

100 mg (0.28 mmol) of the compound obtained in Preparation Example <1-3> was dissolved in 3 mL of tetrahydrofuran, and then 78 μl (0.56 mmol, 2 eq) of triethylamine and 60 μl (0.42 mmol, 1.5 eq) of benzyl chloroformate were added and stirred at room temperature for 2 hours. The solvent was removed under reduced pressure, and the residue was dissolved again in 50 mL of ethyl acetate, and then the organic layer was washed with distilled water three times. The organic layer was dried with anhydrous sodium sulfate and filtered, and the residue obtained by concentrating the filtrate under reduced pressure was purified by silica column chromatography (acetone:methylene chloride=1:4) to give 137 mg of a yellow foam solid compound (yield: 61%).

$^1$H-NMR (300 MHz, CDCl$_3$) δ 1.71-1.79 (m, 1H), 2.25-2.53 (m, 3H), 3.64 (s, 3H), 3.90 (s, 3H), 3.94 (s, 3H), 3.98 (s, 3H), 4.43-4.47 (m, 1H), 4.91 (d, 1H, J=12.3 Hz), 5.07 (d, 1H, J=12.3 Hz), 5.38 (d, 1H, J=7.2 Hz), 6.53 (s, 1H), 6.89 (d, 1H, J=10.8 Hz), 7.28-7.36 (m, 6H), 7.52 (s, 1H)

MS (m/e, M+): 491

EXAMPLE 2

Preparation of (1,2,3,10-tetramethoxy-9-oxo-5,6,7,9-tetrahydro-benzo[a]heptalen-7-yl)-carbamic acid 4-nitro benzyl ester (Compound 2)

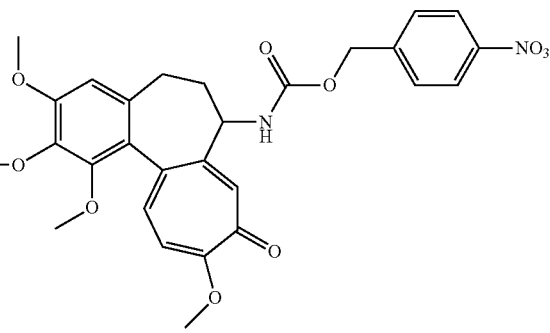

100 mg (0.28 mmol) of the compound obtained in Preparation Example <1-3> was dissolved in 3 mL of tetrahydrofuran, and then 78 μl (0.56 mmol, 2 eq) of triethylamine and 90 μl (0.42 mmol, 1.5 eq) of 4-nitro benzyl chloroformate were added and stirred at room temperature for 2 hours. The solvent was removed under reduced pressure, and the residue was dissolved again in 50 mL of ethyl acetate, and then the organic layer was washed with distilled water three times. The organic layer was dried with anhydrous sodium sulfate and filtered, and the residue obtained by concentrating the filtrate under reduced pressure was purified by silica column chromatography (acetone:methylene chloride=1:4) to give 100 mg of a yellow foam solid compound (yield: 67%).

$^1$H-NMR (300 MHz, CDCl$_3$) δ=1.79-1.80 (m, 1H), 2.29-2.56 (m, 3H), 3.63 (s, 3H), 3.90 (s, 3H), 3.93 (s, 3H), 3.99 (s, 3H), 4.43-4.47 (m, 1H), 5.01 (d, 1H, J=13.5 Hz), 5.15 (d, 1H, J=13.2 Hz), 5.56 (d, 1H, J=7.2 Hz), 6.54 (s, 1H), 6.82 (d, 1H, J=10.8 Hz), 7.29 (d, 1H, J=10.8 Hz), 7.43 (d, 2H, J=8.7 Hz), 7.51 (s, 1H), 8.18 (d, 2H, J=8.7 Hz)

MS (m/e, M+): 536

EXAMPLE 3

Preparation of (1,2,3,10-tetramethoxy-9-oxo-5,6,7,9-tetrahydro-benzo[a]heptalen-7-yl)-carbamic acid 4-bromo benzyl ester (Compound 3)

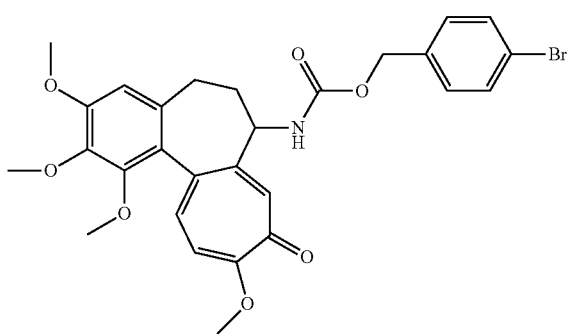 [SMILES: COc1cc2c(c(OC)c1OC)-c1ccc(OC)c(=O)cc1C(NC(=O)OCc1ccc(Br)cc1)CC2]

157 mg (0.84 mmol) of 4-bromobenzyl alcohol was dissolved in 8 mL of tetrahydrofuran, and then 2.2 mL (1.40 mmol) of a 20% phosgene solution was added at 0° C. and stirred at room temperature for 24 hours. The solvent was removed under reduced pressure, and then the residue and 100 mg (0.28 mmol) of the compound prepared in Preparation Example <1-3> were dissolved in 10 mL of tetrahydrofuran. Then, 116 μl (0.84 mmol, 3 eq) of triethylamine was added and stirred at room temperature for 2 hours. The solvent was removed under reduced pressure, the residue was dissolved again in 50 mL of ethyl acetate, and then the organic layer was washed with distilled water three times. The organic layer was dried with anhydrous sodium sulfate and filtered, and the residue obtained by concentrating the filtrate under reduced pressure was purified by silica column chromatography (acetone:methylene chloride=1:4) to give 54 mg of a yellow foam solid compound (yield: 34%).

$^1$H-NMR (300 MHz, CDCl$_3$) δ 1.84-1.90 (m, 1H), 2.33-2.54 (m, 3H), 3.68 (s, 3H), 3.88 (s, 3H), 3.91 (s, 3H), 3.95 (s, 3H), 4.42-4.50 (m, 1H), 4.78 (d, 1H, J=12.3 Hz), 4.98 (d, 1H, J=12 Hz), 6.24 (d, 1H, J=6.9 Hz), 6.55 (s, 1H), 6.80 (d, 1H, J=10.8 Hz), 7.08 (d, 2H, J=8.4 Hz), 7.29 (d, 1H, J=11.7 Hz), 7.39 (d, 2H, J=8.4 Hz), 7.63 (s, 1H)

MS (m/e, M+): 571

EXAMPLE 4

Preparation of (1,2,3,10-tetramethoxy-9-oxo-5,6,7,9-tetrahydro-benzo[a]heptalen-7-yl)-carbamic acid 4-fluoro benzyl ester (Compound 4)

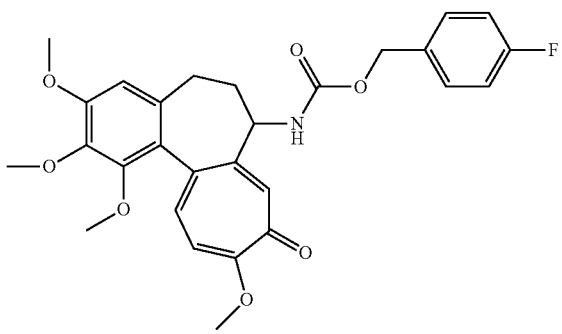 [SMILES: COc1cc2c(c(OC)c1OC)-c1ccc(OC)c(=O)cc1C(NC(=O)OCc1ccc(F)cc1)CC2]

105 mg (0.84 mmol) of 4-fluorobenzyl alcohol was dissolved in 8 mL of tetrahydrofuran, and then 2.2 mL (1.40 mmol) of a 20% phosgene solution was added at 0° C. and stirred at room temperature for 24 hours. The solvent was removed under reduced pressure, and then the residue and 100 mg (0.28 mmol) of the compound prepared in Preparation Example <1-3> were dissolved in 10 mL of tetrahydrofuran. Then, 116 μl (0.84 mmol, 3 eq) of triethylamine was added and stirred at room temperature for 2 hours. The solvent was removed under reduced pressure, the residue was dissolved again in 50 mL of ethyl acetate, and then the organic layer was washed with distilled water three times. The organic layer was dried with anhydrous sodium sulfate and filtered, and the residue obtained by concentrating the filtrate under reduced pressure was purified by silica column chromatography (acetone:methylene chloride=1:4) to give 110 mg of a yellow foam solid compound (yield: 77%).

$^1$H-NMR (300 MHz, CDCl$_3$) δ 1.72-1.74 (m, 1H), 2.27-2.51 (m, 3H), 3.64 (s, 3H), 3.90 (s, 3H), 3.94 (s, 3H), 3.99 (s, 3H), 4.42-4.46 (m, 1H), 4.88 (d, 1H, J=12 Hz), 5.03 (d, 1H, J=12 Hz), 5.25 (d, 1H, J=7.2 Hz), 6.53 (s, 1H), 6.81 (d, 1H, J=10.8 Hz), 7.02 (t, 2H), 7.28-7.29 (m, 3H), 7.48 (s, 1H)

MS (m/e, M+): 509

EXAMPLE 5

Preparation of (1,2,3,10-tetramethoxy-9-oxo-5,6,7,9-tetrahydro-benzo[a]heptalen-7-yl)-carbamic acid 2-fluoro benzyl ester (Compound 5)

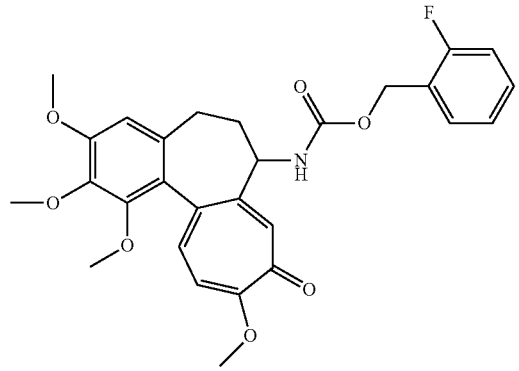 [SMILES: COc1cc2c(c(OC)c1OC)-c1ccc(OC)c(=O)cc1C(NC(=O)OCc1ccccc1F)CC2]

106 mg (0.84 mmol) of 2-fluorobenzyl alcohol was dissolved in 8 mL of tetrahydrofuran, and then 2.2 mL (1.40 mmol) of a 20% phosgene solution was added at 0° C. and stirred at room temperature for 24 hours. The solvent was removed under reduced pressure, and then the residue and 100 mg (0.28 mmol) of the compound prepared in Preparation Example <1-3> were dissolved in 10 mL of tetrahydrofuran. Then, 116 μl (0.84 mmol, 3 eq) of triethylamine was added and stirred at room temperature for 2 hours. The solvent was removed under reduced pressure, the residue was dissolved again in 50 mL of ethyl acetate, and then the organic layer was washed with distilled water three times. The organic layer was dried with anhydrous sodium sulfate and filtered, and the residue obtained by concentrating the filtrate under reduced pressure was purified by silica column chromatography (acetone:methylene chloride=1:4) to give 106 mg of a yellow foam solid compound (yield: 75%).

$^1$H-NMR (300 MHz, CDCl$_3$) δ 1.61-1.79 (m, 1H), 2.26-2.56 (m, 3H), 3.64 (s, 3H), 3.90 (s, 3H), 3.94 (s, 3H), 3.99 (s, 3H), 4.20-4.50 (m, 1H), 4.97 (d, 1H, J=12.3 Hz), 5.17 (d, 1H, J=12.3 Hz), 5.35 (d, 1H, J=7.2 Hz), 6.53 (s, 1H), 6.81 (d, 1H, J=10.8 Hz), 7.00-7.14 (m, 2H), 7.26-7.35 (m, 3H), 7.51 (s, 1H)

MS (m/e, M+): 509

EXAMPLE 6

Preparation of (1,2,3,10-tetramethoxy-9-oxo-5,6,7,9-tetrahydro-benzo[a]heptalen-7-yl)-carbamic acid 3-fluoro benzyl ester (Compound 6)

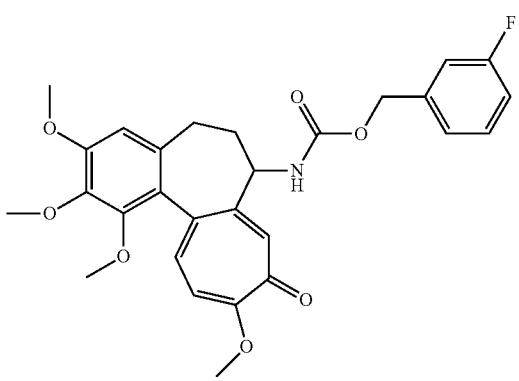 [SMILES: COc1cc2c(c(OC)c1OC)-c1ccc(OC)c(=O)cc1C(NC(=O)OCc1cccc(F)c1)CC2]

106 mg (0.84 mmol) of 3-fluorobenzyl alcohol was dissolved in 8 mL of tetrahydrofuran, and then 2.2 mL (1.40 mmol) of a 20% phosgene solution was added at 0° C. and stirred at room temperature for 24 hours. The solvent was removed under reduced pressure, and then the residue and 100 mg (0.28 mmol) of the compound prepared in Preparation Example <1-3> were dissolved in 10 mL of tetrahydrofuran. Then, 116 μl (0.84 mmol, 3 eq) of triethylamine was added and stirred at room temperature for 2 hours. The solvent was removed under reduced pressure, the residue was dissolved again in 50 mL of ethyl acetate, and then the organic layer was washed with distilled water three times. The organic layer was dried with anhydrous sodium sulfate and filtered, and the residue obtained by concentrating the filtrate under reduced pressure was purified by silica column chromatography (acetone:methylene chloride=1:4) to give 115 mg of a yellow foam solid compound (yield: 81%).

$^1$H-NMR (300 MHz, CDCl$_3$) δ 1.74-1.84 (m, 1H), 2.26-2.56 (m, 3H), 3.62 (s, 3H), 3.90 (s, 3H), 3.94 (s, 3H), 3.99 (s, 3H), 4.18-4.50 (m, 1H), 4.86 (d, 1H, J=12.6 Hz), 5.07 (d, 1H, J=12.3 Hz), 5.59 (d, 1H, J=7.5 Hz), 6.54 (s, 1H), 6.81 (d, 1H, J=10.5 Hz), 7.95-7.05 (m, 2H), 7.24-7.32 (m, 3H), 7.54 (s, 1H)

MS (m/e, M+): 509

EXAMPLE 7

Preparation of (1,2,3,10-tetramethoxy-9-oxo-5,6,7,9-tetrahydro-benzo[a]heptalen-7-yl)-carbamic acid 4-methoxy benzyl ester (Compound 7)

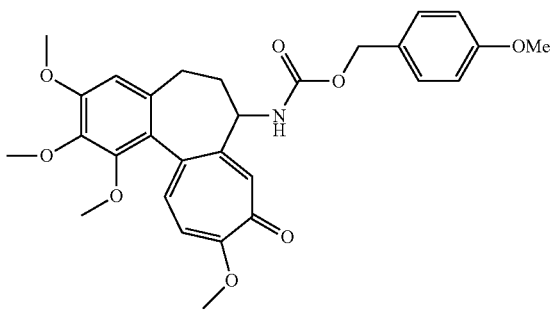 [SMILES: COc1ccc(COC(=O)NC2CCc3cc(OC)c(OC)c(OC)c3-c3ccc(OC)c(=O)cc32)cc1]

116 mg (0.84 mmol) of 4-methoxybenzyl alcohol was dissolved in 8 mL of tetrahydrofuran, and then 2.2 mL (1.40 mmol) of a 20% phosgene solution was added at 0° C. and stirred at room temperature for 24 hours. The solvent was removed under reduced pressure, and then the residue and 100 mg (0.28 mmol) of the compound prepared in Preparation Example <1-3> were dissolved in 10 mL of tetrahydrofuran. Then, 116 μl (0.84 mmol, 3 eq) of triethylamine was added and stirred at room temperature for 2 hours. The solvent was removed under reduced pressure, the residue was dissolved again in 50 mL of ethyl acetate, and then the organic layer was washed with distilled water three times. The organic layer was dried with anhydrous sodium sulfate and filtered, and the residue obtained by concentrating the filtrate under reduced pressure was purified by silica column chromatography (acetone:methylene chloride=1:4) to give 68 mg of a yellow foam solid compound (yield: 47%).

$^1$H-NMR (300 MHz, CDCl$_3$) δ 1.68-1.78 (m, 1H), 2.22-2.55 (m, 3H), 3.65 (s, 3H), 3.77 (s, 3H), 3.90 (s, 3H), 3.94 (s, 3H), 3.98 (s, 3H), 4.40-4.49 (m, 1H), 4.83 (d, 1H, J=11.7 Hz), 5.01 (d, 1H, J=11.7 Hz), 5.35 (d, 1H, J=7.2 Hz), 6.53 (s, 1H), 6.79-6.87 (m, 3H), 7.21-7.29 (m, 3H), 7.51 (s, 1H)

MS (m/e, M+): 521

EXAMPLE 8

Preparation of (1,2,3,10-tetramethoxy-9-oxo-5,6,7,9-tetrahydro-benzo[a]heptalen-7-yl)-carbamic acid 4-methyl benzyl ester (Compound 8)

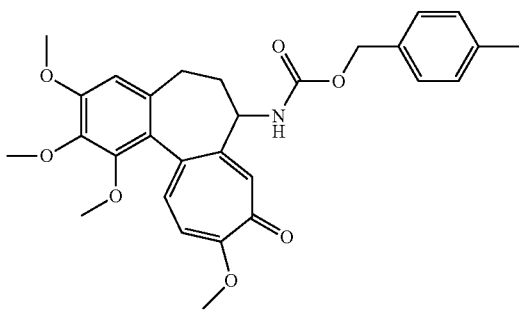

102 mg (0.84 mmol) of 4-methylbenzyl alcohol was dissolved in 8 mL of tetrahydrofuran, and then 2.2 mL (1.40 mmol) of a 20% phosgene solution was added at 0° C. and stirred at room temperature for 24 hours. The solvent was removed under reduced pressure, and then the residue and 100 mg (0.28 mmol) of the compound prepared in Preparation Example <1-3> were dissolved in 10 mL of tetrahydrofuran. Then, 116 μl (0.84 mmol, 3 eq) of triethylamine was added and stirred at room temperature for 2 hours. The solvent was removed under reduced pressure, the residue was dissolved again in 50 mL of ethyl acetate, and then the organic layer was washed with distilled water three times. The organic layer was dried with anhydrous sodium sulfate and filtered, and the residue obtained by concentrating the filtrate under reduced pressure was purified by silica column chromatography (acetone:methylene chloride=1:4) to give 93 mg of a yellow foam solid compound (yield: 66%).

$^1$H-NMR (300 MHz, CDCl$_3$) δ 1.70-1.78 (m, 1H), 2.17-2.55 (m, 6H), 3.64 (s, 3H), 3.90 (s, 3H), 3.94 (s, 3H), 3.99 (s, 3H), 4.40-4.49 (m, 1H), 4.86 (d, 1H, J=12 Hz), 5.03 (d, 1H, J=12 Hz), 5.31 (d, 1H, J=7.5 Hz), 6.53 (s, 1H), 6.81 (d, 1H, J=10.8 Hz), 7.07-7.29 (m, 5H), 7.51 (s, 1H)

MS (m/e, M+): 505

EXAMPLE 9

Preparation of (1,2,3,10-tetramethoxy-9-oxo-5,6,7,9-tetrahydro-benzo[a]heptalen-7-yl)-carbamic acid 4-isopropyl benzyl ester (Compound 9)

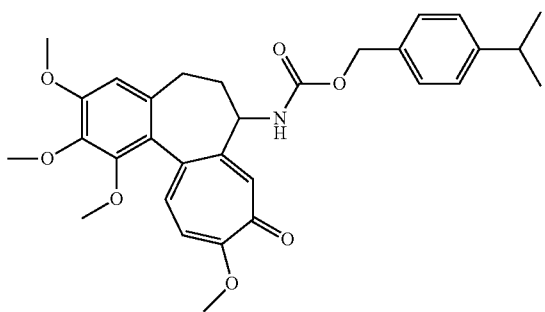 [SMILES: COc1cc2c(c(OC)c1OC)-c1ccc(OC)c(=O)cc1C(NC(=O)OCc1ccc(C(C)C)cc1)CC2]

126 mg (0.84 mmol) of 4-isopropyl benzyl alcohol was dissolved in 8 mL of tetrahydrofuran, and then 2.2 mL (1.40 mmol) of a 20% phosgene solution was added at 0° C. and stirred at room temperature for 24 hours. The solvent was removed under reduced pressure, and then the residue and 100 mg (0.28 mmol) of the compound prepared in Preparation Example <1-3> were dissolved in 10 mL of tetrahydrofuran. Then, 116 μl (0.84 mmol, 3 eq) of triethylamine was added and stirred at room temperature for 2 hours. The solvent was removed under reduced pressure, the residue was dissolved again in 50 mL of ethyl acetate, and then the organic layer was washed with distilled water three times. The organic layer was dried with anhydrous sodium sulfate and filtered, and the residue obtained by concentrating the filtrate under reduced pressure was purified by silica column chromatography (acetone:methylene chloride=1:4) to give 121 mg of a yellow foam solid compound (yield: 81%).

$^1$H-NMR (300 MHz, CDCl$_3$) δ 1.23 (d, 6H, J=3.9 Hz), 1.69-1.78 (m, 1H), 2.23-2.55 (m, 3H), 2.84-2.93 (m, 1H), 3.64 (s, 3H), 3.90 (s, 3H), 3.94 (s, 3H), 3.98 (s, 3H), 4.41-4.49 (m, 1H), 4.86 (d, 1H, J=12 Hz), 5.04 (d, 1H, J=12 Hz), 5.37 (d, 1H, J=7.2 Hz), 6.53 (s, 1H), 6.81 (d, 1H, J=10.8 Hz), 7.12-7.30 (m, 5H), 7.52 (s, 1H)

MS (m/e, M+): 533

EXAMPLE 10

Preparation of (1,2,3,10-tetramethoxy-9-oxo-5,6,7,9-tetrahydro-benzo[a]heptaen-7-yl)-carbamic acid cyclopentyl methyl ester (Compound 10)

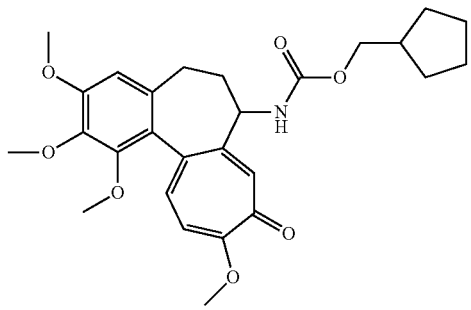 [SMILES: COc1cc2c(c(OC)c1OC)-c1ccc(OC)c(=O)cc1C(NC(=O)OCC1CCCC1)CC2]

84 mg (0.84 mmol) of cyclopentane methanol was dissolved in 8 mL of tetrahydrofuran, and then 2.2 mL (1.40 mmol) of a 20% phosgene solution was added at 0° C. and stirred at room temperature for 24 hours. The solvent was removed under reduced pressure, and then the residue and 100 mg (0.28 mmol) of the compound obtained in Preparation Example <1-3> was dissolved in 10 mL of tetrahydrofuran. Then, 116 μl (0.84 mmol, 3 eq) of triethylamine was added and stirred at room temperature for 2 hours. The solvent was removed under reduced pressure, the residue was dissolved again in 50 mL of ethyl acetate, and then the organic layer was washed with distilled water three times. The organic layer was dried with anhydrous sodium sulfate and filtered, and the residue obtained by concentrating the filtrate under reduced pressure was purified by silica column chromatography (acetone:methylene chloride=1:4) to give 105 mg of a yellow foam solid compound (yield: 78%).

$^1$H-NMR (300 MHz, CDCl$_3$) δ 1.17-1.25 (m, 2H), 1.48-1.78 (m, 6H), 2.09-2.17 (m, 1H), 2.26-2.56 (m, 3H), 3.62 (s, 3H), 3.78-3.86 (m, 2H), 3.90 (s, 3H), 3.92 (s, 3H), 3.93 (s, 3H), 3.99-4.44 (m, 1H), 5.17 (d, 1H, J=7.5 Hz), 6.53 (s, 1H), 6.80 (d, 1H, J=11.1 Hz), 7.27 (d, 1H, J=10.5 Hz), 7.48 (s, 1H)

MS (m/e, M+): 483

EXAMPLE 11

Preparation of (1,2,3,10-tetramethoxy-9-oxo-5,6,7,9-tetrahydro-benzo[a]heptalen-7-yl)-carbamic acid cyclohexylmethyl ester (Compound 11)

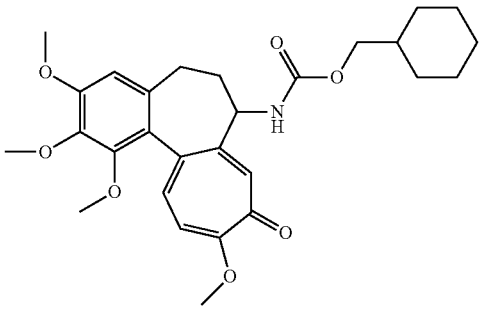 [SMILES: COc1cc2c(c(OC)c1OC)-c1ccc(OC)c(=O)cc1C(NC(=O)OCC1CCCCC1)CC2]

96 mg (0.84 mmol) of cyclohexyl methanol was dissolved in 8 mL of tetrahydrofuran, and then 2.2 mL (1.40 mmol) of a 20% phosgene solution was added at 0° C. and stirred at room temperature for 24 hours. The solvent was removed under reduced pressure, and then the residue and 100 mg (0.28 mmol) of the compound obtained in Preparation Example <1-3> was dissolved in 10 mL of tetrahydrofuran. Then, 116 μl (0.84 mmol, 3 eq) of triethylamine was added and stirred at room temperature for 2 hours. The solvent was removed under reduced pressure, the residue was dissolved again in 50 mL of ethyl acetate, and then the organic layer was washed with distilled water three times. The organic layer was dried with anhydrous sodium sulfate and filtered, and the residue obtained by concentrating the filtrate under reduced pressure was purified by silica column chromatography (acetone:methylene chloride=1:4) to give 109 mg of a yellow foam solid compound (yield: 78%).

$^1$H-NMR (300 MHz, CDCl$_3$) δ 0.88-0.95 (m, 2H), 1.10-1.27 (m, 3H), 1.54-1.78 (m, 6H), 2.24-2.56 (m, 3H), 3.62 (s, 3H), 3.69-3.82 (m, 2H) 3.90 (s, 3H), 3.92 (s, 3H), 3.99 (s, 3H), 4.38-4.47 (m, 1H), 5.19 (d, 1H, J=7.5 Hz), 6.53 (s, 1H), 6.80 (d, 1H, J=11.1 Hz), 7.27 (d, 1H, J=10.5 Hz), 7.48 (s, 1H)

MS (m/e, M+): 497

EXAMPLE 12

Preparation of (1,2,3,10-tetramethoxy-9-oxo-5,6,7,9-tetrahydro-benzo[a]heptalen-7-yl)-carbamic acid indan-1-ylmethyl ester (Compound 12)

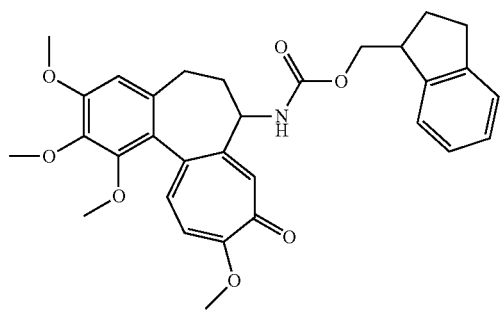 [SMILES: COc1cc2c(c(OC)c1OC)-c1ccc(OC)c(=O)cc1C(NC(=O)OCC1CCc3ccccc31)CC2]

124 mg (0.84 mmol) of the compound obtained in Preparation Example <2-1> was dissolved in 8 mL of tetrahydrofuran, and then 2.2 mL (4.20 mmol) of a 20% phosgene solution was added at 0° C. and stirred at room temperature for 24 hours. The solvent was removed under reduced pressure, and then the residue and 100 mg (0.28 mmol) of the compound prepared in Preparation Example <1-3> were dissolved in 10 mL of tetrahydrofuran. Then, 116 μl (0.78 mmol, 2 eq) of triethylamine was added and stirred at room temperature for 2 hours. The solvent was removed under reduced pressure, the residue was dissolved again in 50 mL of ethyl acetate, and then the organic layer was washed with distilled water three times. The organic layer was dried with anhydrous sodium sulfate and filtered, and the residue obtained by concentrating the filtrate under reduced pressure was purified by silica column chromatography (acetone:methylene chloride=1:4) to give 121 mg of a yellow foam solid compound (yield: 81%).

$^1$H-NMR (300 MHz, CDCl$_3$) δ 1.73-1.83 (m, 2H), 2.14-2.56 (m, 4H), 2.82-2.90 (m, 2H), 3.31-3.35 (m, 1H), 3.58 (s, 3H), 3.90 (s, 3H), 3.93 (s, 3H), 3.98-4.02 (m, 4H), 4.17-4.22 (m, 1H), 4.43-4.47 (m, 1H), 5.62 (d, 1H, J=6 Hz), 6.54 (s, 1H), 6.81 (d, 1H, J=12 Hz), 7.12-7.29 (m, 5H), 7.57 (s, 1H)

MS (m/e, M+): 531

EXAMPLE 13

Preparation of (1,2,3,10-tetramethoxy-9-oxo-5,6,7,9-tetrahydro-benzo[a]heptalen-7-yl)-carbamic acid 1,2,3,4-tetrahydro-naphthalen-1-ylmethyl ester (Compound 13)

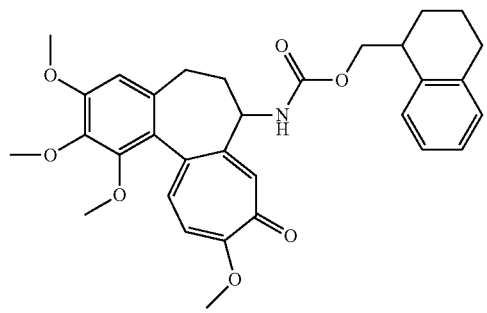 [SMILES: COc1cc2c(c(OC)c1OC)-c1ccc(OC)c(=O)cc1C(NC(=O)OCC1CCCc3ccccc31)CC2]

136 mg (0.84 mmol) of the compound obtained in Preparation Example <2-2> was dissolved in 8 mL of tetrahydrofuran, and then 2.2 mL (4.20 mmol) of a 20% phosgene solution was added at 0° C. and stirred at room temperature for 24 hours. The solvent was removed under reduced pressure, and then the residue and 100 mg (0.28 mmol) of the compound prepared in Preparation Example <1-3> were dissolved in 10 mL of tetrahydrofuran. Then, 116 μl (0.78 mmol, 2 eq) of triethylamine was added and stirred at room temperature for 2 hours. The solvent was removed under reduced pressure, the residue was dissolved again in 50 mL of ethyl acetate, and then the organic layer was washed with distilled water three times. The organic layer was dried with anhydrous sodium sulfate and filtered, and the residue obtained by concentrating the filtrate under reduced pressure was purified by silica column chromatography (acetone:methylene chloride=1:4) to give 140 mg of a yellow foam solid compound (yield: 92%).

$^1$H-NMR (300 MHz, CDCl$_3$) δ 1.65-1.79 (m, 4H), 2.26-2.57 (m, 4H), 2.72-2.74 (m, 2H), 2.97-3.05 (m, 1H), 3.63 (s, 3H), 3.90 (s, 3H), 3.93-3.95 (4H; s, 3H & m, 1H), 3.99 (s, 3H), 4.22-4.27 (m, 1H), 4.41-4.47 (m, 1H), 5.37-5.39 (d, 1H, J=7.4 Hz), 6.54 (s, 1H), 6.79-6.84 (d, 1H, J=10.8 Hz), 7.01-7.16 (m, 4H), 7.25-7.29 (d, 1H, J=10.8 Hz), 7.52 (s, 1H)

MS (m/e, M+): 545

EXAMPLE 14

Preparation of (1,2,3,10-tetramethoxy-9-oxo-5,6,7,9-tetrahydro-benzo[a]heptalen-7-yl)-carbamic acid 9H-fluoren-9-ylmethyl ester (Compound 14)

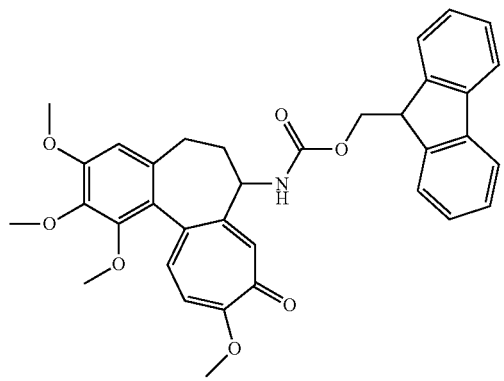 [SMILES: COc1cc2c(c(OC)c1OC)-c1ccc(OC)c(=O)cc1C(NC(=O)OCC1c3ccccc3-c3ccccc31)CC2]

100 mg (0.28 mmol) of the compound obtained in Preparation Example <1-3> was dissolved in 10 mL of tetrahydrofuran, and then 58 μl (0.4 mmol) of triethylamine and 86 mg (0.32 mmol) of 9-fluorenylmethyl chloroformate were added and stirred at room temperature for 2 hours. The solvent was removed under reduced pressure, and the residue was dissolved again in 50 mL of ethyl acetate, and then the organic layer was washed with distilled water three times. The organic layer was dried with anhydrous sodium sulfate and filtered, and the residue obtained by concentrating the filtrate under reduced pressure was purified by silica column chromatography (acetone:methylene chloride=1:4) to give 155 mg of a yellow foam solid compound (yield: 96%).

$^1$H-NMR (300 MHz, CDCl$_3$) δ 2.00-2.05 (m, 1H), 2.39-2.57 (m, 3H), 3.28 (s, 3H), 3.78-4.03 (m, 11H), 4.41-4.56 (m, 2H), 6.54 (s, 1H), 6.70-6.76 (m, 2H), 7.17-7.39 (m, 5H), 7.49-7.56 (m, 2H), 7.69-7.71 (d, 2H, J=6.7 Hz), 7.86 (s, 1H)

MS (m/e, M+): 579

EXAMPLE 15

Preparation of (1,2,3,10-tetramethoxy-9-oxo-5,6,7,9-tetrahydro-benzo[a]heptalen-7-yl)-carbamic acid 1-methyl-9H-fluoren-9-ylmethyl ester (Compound 15)

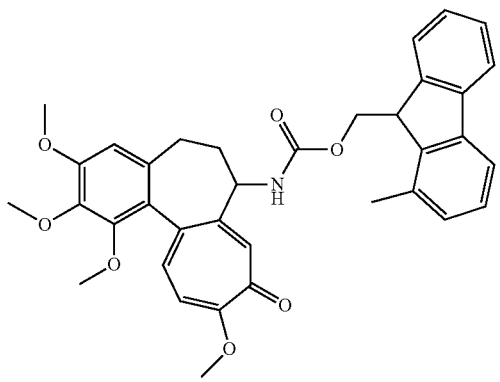 [SMILES: COc1cc2c(c(OC)c1OC)-c1ccc(OC)c(=O)cc1C(NC(=O)OCC1c3ccccc3-c3cccc(C)c31)CC2]

176 mg (0.84 mmol) of (1-methyl-9H-fluoren-9-yl)-methanol was dissolved in 8 mL of tetrahydrofuran, and then 2.2 mL (4.20 mmol) of a 20% phosgene solution was added at 0° C. and stirred at room temperature for 1 hour. The solvent was removed under reduced pressure, and then the residue and 100 mg (0.28 mmol) of the compound prepared in Preparation Example <1-3> were dissolved in 10 mL of tetrahydrofuran. Then, 116 μl (0.84 mmol, 3 eq) of triethylamine was added and stirred at room temperature for 2 hours. The solvent was removed under reduced pressure, the residue was dissolved again in 50 mL of ethyl acetate, and then the organic layer was washed with distilled water three times. The organic layer was dried with anhydrous sodium sulfate and filtered, and the residue obtained by concentrating the filtrate under reduced pressure was purified by silica column chromatography (methanol:methylene chloride=1:19) to give 41 mg of a yellow foam solid compound (yield: 33%).

$^1$H-NMR (300 MHz, CDCl$_3$) δ 1.77 (m, 1H), 2.23 (m, 3H), 2.45 (s, 3H), 3.58 (s, 3H), 3.90 (s, 3H), 3.92 (s, 3H), 3.99 (s, 3H), 4.08 (m, 2H), 4.44 (m, 1H), 4.71 (dd, 1H), 5.40 (m, NH), 6.53 (s, 1H), 6.78 (m, 1H), 7.05 (t, 1H), 7.07 (m, 4H), 7.46 (s, 1H), 7.62 (m, 2H), 7.70 (d, 1H)

MS (m/e, M+): 593

EXAMPLE 16

Preparation of (1,2,3,10-tetramethoxy-9-oxo-5,6,7,9-tetrahydro-benzo[a]heptalen-7-yl)-carbamic acid 2-bromo-9H-fluoren-9-ylmethyl ester (Compound 16)

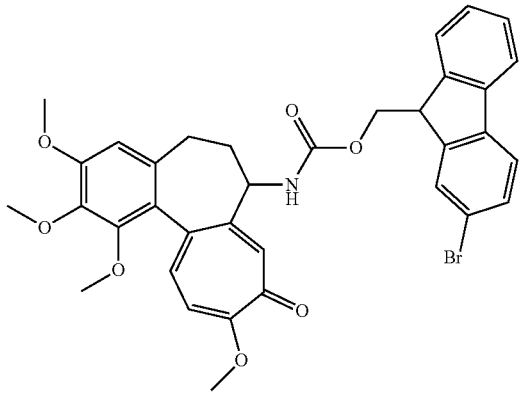 [SMILES: COc1cc2c(c(OC)c1OC)-c1ccc(OC)c(=O)cc1C(NC(=O)OCC1c3ccccc3-c3ccc(Br)cc31)CC2]

231 mg (0.84 mmol) of (2-bromo-9H-fluoren-9-yl)-methanol was dissolved in 8 mL of tetrahydrofuran, and then 2.2 mL (4.20 mmol) of a 20% phosgene solution was added at 0° C. and stirred at room temperature for 1 hour. The solvent was removed under reduced pressure, and then the residue and 100 mg (0.28 mmol) of the compound prepared in Preparation Example <1-3> were dissolved in 10 mL of tetrahydrofuran. Then, 116 μl (0.84 mmol, 3 eq) of triethylamine was added and stirred at room temperature for 2 hours. The solvent was removed under reduced pressure, the residue was dissolved again in 50 mL of ethyl acetate, and then the organic layer was washed with distilled water three times. The organic layer was dried with anhydrous sodium sulfate and filtered, and the residue obtained by concentrating the filtrate under reduced pressure was purified by silica column chromatography (methanol:methylene chloride=1:19) to give 70 mg of a yellow foam solid compound (yield: 39%).

$^1$H-NMR (300 MHz, CDCl$_3$) δ 2.05 (m, 1H), 2.39 (m, 3H), 3.66 (s, 3H), 3.90 (s, 3H), 3.91 (s, 3H), 3.97 (m, 4H), 4.21 (m, 1H), 4.44 (m, 2H), 5.84 (m, NH), 6.55 (s, 1H), 6.77 (d, 1H), 7.25 (m, 2H), 7.51 (m, 7H)

MS (m/e, M+): 658

EXAMPLE 17

Preparation of (1,2,3,10-tetramethoxy-9-oxo-5,6,7,9-tetrahydro-benzo[a]heptalen-7-yl)-carbamic acid 2,7-di-tert-butyl-9H-fluoren-9-ylmethyl ester (Compound 17)

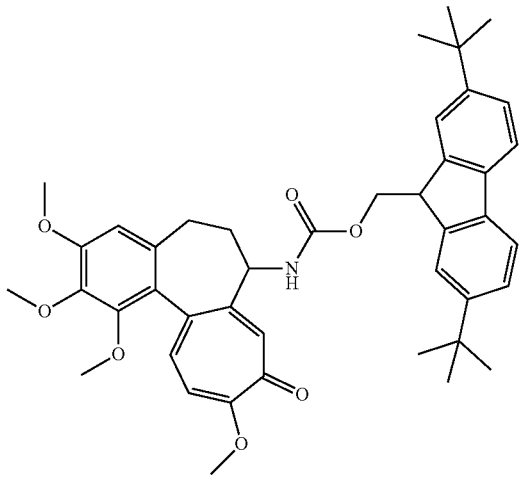 [SMILES: COc1cc2c(c(OC)c1OC)-c1ccc(OC)c(=O)cc1C(NC(=O)OCC1c3cc(C(C)(C)C)ccc3-c3ccc(C(C)(C)C)cc31)CC2]

100 mg (0.28 mmol) of the compound obtained in Preparation Example <1-3> was dissolved in 3 mL of tetrahydrofuran, and then 116 μl (0.84 mmol) of triethylamine and 156 mg (0.42 mmol) of 2,7 di-tert-butyl-9-fluorenylmethyl chloroformate were added and stirred at room temperature for 2 hours. The solvent was removed under reduced pressure, the residue was dissolved again in 50 mL of ethyl acetate, and then the organic layer was washed with distilled water three times. The organic layer was dried with anhydrous sodium sulfate and filtered, and the residue obtained by concentrating the filtrate under reduced pressure was purified by silica column chromatography (acetone:methylene chloride=1:4) to give 174 mg of a yellow foam solid compound (yield: 90%).

$^1$H-NMR (300 MHz, CDCl$_3$) δ 1.31 (s, 9H), 1.34 (s, 9H), 1.76-1.84 (m, 1H), 2.22-2.56 (m, 3H), 3.59 (s, 3H), 3.90 (s, 3H), 3.92 (s, 3H), 3.98 (s, 3H), 4.02-4.07 (m, 1H), 4.30-4.34 (m, 2H), 4.41-4.49 (m, 1H), 5.43-5.45 (d, 1H, J=7.4 Hz), 6.53 (s, 1H), 6.78-6.82 (d, 1H, J=10.8 Hz), 7.25-7.28 (m, 1H), 7.37-7.39 (d, 2H, J=8 Hz), 7.50-7.66 (m, 5H)

MS (m/e, M+): 691

EXAMPLE 18

Preparation of (1,2,3,10-tetramethoxy-9-oxo-5,6,7,9-tetrahydro-benzo[a]heptalen-7-yl)-carbamic acid 2-(9H-fluoren-9-yl)-ethyl ester (Compound 18)

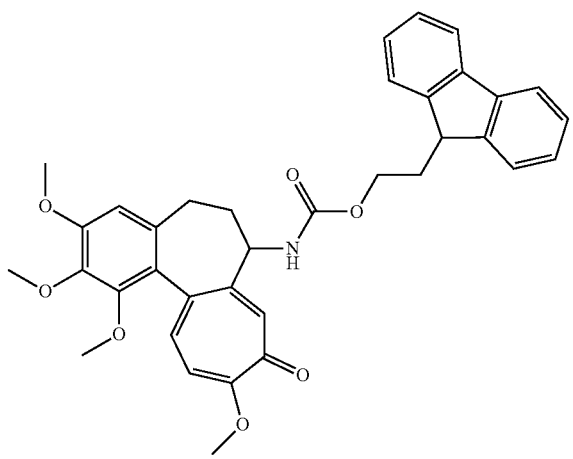 [SMILES: COc1cc2c(c(OC)c1OC)-c1ccc(OC)c(=O)cc1C(NC(=O)OCCC1c3ccccc3-c3ccccc31)CC2]

176 mg (0.84 mmol) of the compound obtained in Preparation Example <2-3> was dissolved in 8 mL of tetrahydrofuran, and then 2.2 mL (1.40 mmol) of a 20% phosgene solution was added at 0° C. and stirred at room temperature for 24 hours. The solvent was removed under reduced pressure, and then the residue and 100 mg (0.28 mmol) of the compound prepared in Preparation Example <1-3> were dissolved in 10 mL of tetrahydrofuran. Then, 116 μl (0.84 mmol) of triethylamine was added and stirred at room temperature for 2 hours. The solvent was removed under reduced pressure, the residue was dissolved again in 50 mL of ethyl acetate, and then the organic layer was washed with distilled water three times. The organic layer was dried with anhydrous sodium sulfate and filtered, and the residue obtained by concentrating the filtrate under reduced pressure was purified by silica column chromatography (acetone:methylene chloride=1:4) to give 154 mg of a yellow foam solid compound (yield: 93%).

$^1$H-NMR (300 MHz, CDCl$_3$) δ 1.64-1.74 (m, 1H), 2.18-2.54 (m, 5H), 3.59 (s, 3H), 3.86-3.96 (m, 11H), 4.01-4.06 (t, 1H), 4.30-4.38 (m, 1H), 5.05-5.08 (d, 1H, J=6.7 Hz), 6.53 (s, 1H), 6.76-6.80 (d, 1H, J=10.9 Hz), 7.21-7.37 (m, 5H), 7.44-7.49 (m, 3H), 7.72-7.75 (d, 2H, J=7.3 Hz)

MS (m/e, M+): 593

EXAMPLE 19

Preparation of 2-phenyl-N-(1,2,3,10-tetramethoxy-9-oxo-5,6,7,9-tetrahydro-benzo[a]heptalen-7-yl)-acetamide (Compound 19)

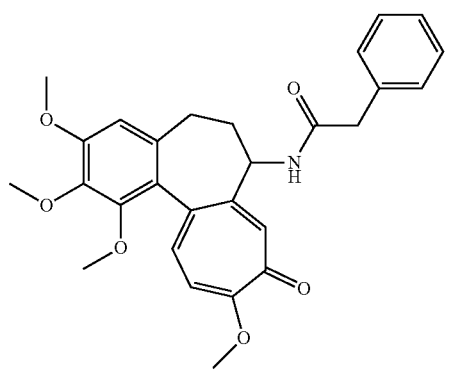 [SMILES: COc1cc2c(c(OC)c1OC)-c1ccc(OC)c(=O)cc1C(NC(=O)Cc1ccccc1)CC2]

100 mg (0.28 mmol) of the compound obtained in Preparation Example <1-3> was dissolved in 8 mL of tetrahydrofuran, and then 116 μl (0.84 mmol) of triethylamine and 65 mg (0.42 mmol) of phenyl acetyl chloride were added and stirred at room temperature for 2 hours. The solvent was removed under reduced pressure, the residue was dissolved again in 50 mL of ethyl acetate, and then the organic layer was washed with distilled water three times. The organic layer was dried with anhydrous sodium sulfate and filtered, and the residue obtained by concentrating the filtrate under reduced pressure was purified by silica column chromatography (acetone:methylene chloride=1:4) to give 113 mg of a yellow foam solid compound (yield: 85%).

$^1$H-NMR (300 MHz, CDCl$_3$) δ 1.61-1.71 (m, 1H), 2.08-2.17 (m, 1H), 2.33-2.51 (m, 2H), 3.56 (s, 2H), 3.65 (s, 3H), 3.89 (s, 3H), 3.93 (s, 3H), 3.99 (s, 3H), 4.59-4.66 (m, 1H), 5.99-5.97 (d, 1H, J=6 Hz), 6.51 (s, 1H), 6.78-6.81 (d, 1H, J=9 Hz), 7.26-7.39 (m, 7H)

MS (m/e, M+): 475

EXAMPLE 20

Preparation of 2-(4-methoxy-phenyl)-N-(1,2,3,10-tetramethoxy-9-oxo-5,6,7,9-tetrahydro-benzo[a]heptalen-7-yl)-acetamide (Compound 20)

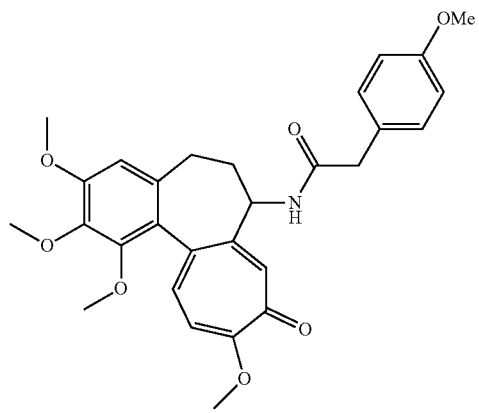 [SMILES: COc1ccc(CC(=O)NC2CCc3cc(OC)c(OC)c(OC)c3-c3ccc(OC)c(=O)cc32)cc1]

100 mg (0.28 mmol) of the compound obtained in Preparation Example <1-3> was dissolved in 8 mL of tetrahydrofuran, and then 116 μl (0.84 mmol) of triethylamine and 77 mg (0.42 mmol) of 4-methoxy acetyl chloride were added and stirred at room temperature for 2 hours. The solvent was removed under reduced pressure, the residue was dissolved again in 50 mL of ethyl acetate, and then the organic layer was washed with distilled water three times. The organic layer was dried with anhydrous sodium sulfate and filtered, and the residue obtained by concentrating the filtrate under reduced pressure was purified by silica column chromatography (acetone:methylene chloride=1:4) to give 100 mg of a yellow foam solid compound (yield: 71%).

$^1$H-NMR (300 MHz, CDCl$_3$) δ 1.67-1.73 (m, 1H), 2.08-2.17 (m, 1H), 2.32-2.51 (m, 2H), 3.57 (s, 2H), 3.66 (s, 3H), 3.80 (s, 3H), 3.88 (s, 3H), 3.93 (s, 3H), 3.98 (s, 3H), 4.56-4.63 (m, 1H), 6.13-6.15 (d, 1H, J=6 Hz), 6.49 (s, 1H), 6.78-6.82 (d, 1H, J=12 Hz), 6.87-6.90 (d, 2H, J=8.7 Hz), 7.16-7.19 (d, 2H, J=8.4 Hz), 7.26-7.30 (d, 1H, J=12 Hz)

MS (m/e, M+): 505

EXAMPLE 21

Preparation of 3-phenyl-N-(1,2,3,10-tetramethoxy-9-oxo-5,6,7,9-tetrahydro-benzo[a]heptalen-7-yl)-propionamide (Compound 21)

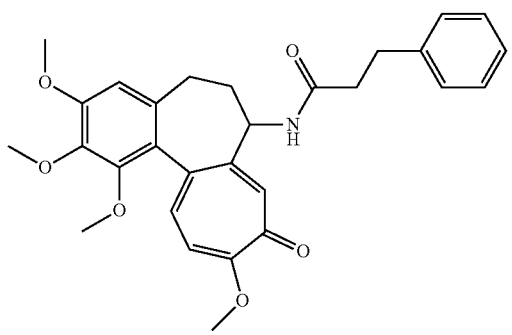 [SMILES: COc1cc2c(c(OC)c1OC)-c1ccc(OC)c(=O)cc1C(NC(=O)CCc1ccccc1)CC2]

100 mg (0.28 mmol) of the compound obtained in Preparation Example <1-3> was dissolved in 3 mL of methylene chloride, and then 80 mg (0.42 mmol) of 1-[3-(dimethylamino) propyl]-3-ethylcarbodiimide (EDC), 18 mg (0.14 mmol) of 1-hydroxybenzotriazole (HOBt), 116 μl (0.84 mmol) of triethylamine, and 62 mg (0.40 mmol) of hydrocinnamic acid were added at 0° C. and stirred at room temperature for 24 hours. The solvent was removed under reduced pressure, the residue was dissolved again in 50 mL of methylene chloride, and then the organic layer was washed with distilled water three times. The organic layer was dried with anhydrous sodium sulfate and filtered, and the residue obtained by concentrating the filtrate under reduced pressure was purified by silica column chromatography (acetone:methylene chloride=1:4) to give 81 mg of a yellow foam solid compound (yield: 59%).

$^1$H-NMR (300 MHz, CDCl$_3$) δ 1.73-1.81 (m, 1H), 2.14-2.22 (m, 1H), 2.32-2.54 (m, 4H), 2.85-2.90 (2, 1H), 3.66 (s, 3H), 3.90 (s, 3H), 3.95 (s, 3H), 3.97 (s, 3H), 4.60-4.69 (m, 1H), 6.52 (s, 1H), 6.63-6.65 (d, 1H, J=6.9 Hz), 6.80-6.84 (d, 1H, J=10.8 Hz), 7.11-7.33 (m, 6H), 7.41 (s, 1H)

MS (m/e, M+): 489

EXAMPLE 22

Preparation of 3-(4-methoxy-phenyl)-N-(1,2,3,10-tetramethoxy-9-oxo-5,6,7,9-tetrahydro-benzo[a]heptalen-7-yl)-propionamide (Compound 22)

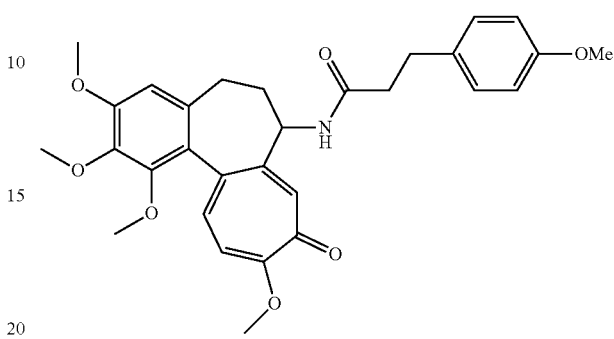

100 mg (0.28 mmol) of the compound obtained in Preparation Example <1-3> was dissolved in 3 mL of methylene chloride, and then 80 mg (0.42 mmol) of 1-[3-(dimethylamino) propyl]-3-ethylcarbodiimide (EDC), 18 mg (0.14 mmol) of 1-hydroxybenzotriazole (HOBt), 116 μl (0.84 mmol) of triethylamine, and 62 mg (0.40 mmol) of 3-(4-methoxyphenyl)propionic acid were added at 0° C. and stirred at room temperature for 24 hours. The solvent was removed under reduced pressure, the residue was dissolved again in 50 mL of methylene chloride, and then the organic layer was washed with distilled water three times. The organic layer was dried with anhydrous sodium sulfate and filtered, and the residue obtained by concentrating the filtrate under reduced pressure was purified by silica column chromatography (acetone:methylene chloride=1:4) to give 131 mg of a yellow foam solid compound (yield: 90%).

$^1$H-NMR (300 MHz, CDCl$_3$) δ 1.72-1.82 (m, 1H), 2.18-2.23 (m, 1H), 2.33-2.51 (m, 4H), 2.80-2.85 (2, 1H), 3.67 (s, 3H), 3.78 (s, 3H), 3.91 (s, 3H), 3.95 (s, 3H), 3.98 (s, 3H), 4.61-4.69 (m, 1H), 6.53 (s, 1H), 6.69-6.85 (m, 4H), 7.03-7.06 (d, 2H, J=9 Hz), 7.27-7.34 (m, 1H), 7.43 (s, 1H)

MS (m/e, M+): 519

EXAMPLE 23

Preparation of 2-(9H-fluoren-9-yl)-N-(1,2,3,10-tetramethoxy-9-oxo-5,6,7,9-tetrahydro-benzo[a]heptalen-7-yl)-acetamide (Compound 23)

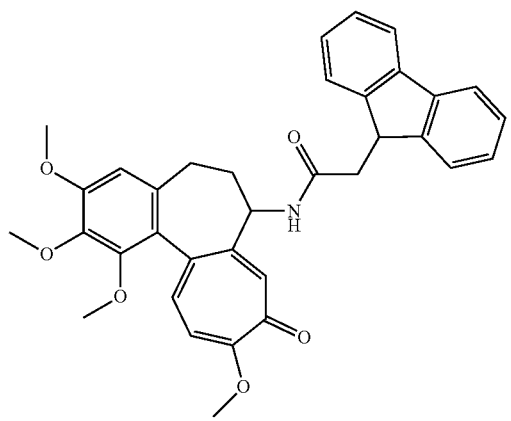 [SMILES: COc1cc2c(c(OC)c1OC)-c1ccc(OC)c(=O)cc1C(NC(=O)CC1c3ccccc3-c3ccccc31)CC2]

100 mg (0.28 mmol) of the compound obtained in Preparation Example <1-3> was dissolved in 3 mL of methylene chloride, and then 80 mg (0.42 mmol) of 1-[3-(dimethylamino)propyl]-3-ethylcarbodiimide (EDC), 18 mg (0.14 mmol) of 1-hydroxybenzotriazole (HOBt), 116 μl (0.84 mmol) of triethylamine, and 94 mg (0.42 mmol) of 9-fluoreneacetic acid were added at 0° C. and stirred at room temperature for 24 hours. The solvent was removed under reduced pressure, the residue was dissolved again in 50 mL of methylene chloride, and then the organic layer was washed with distilled water three times. The organic layer was dried with anhydrous sodium sulfate and filtered, and the residue obtained by concentrating the filtrate under reduced pressure was purified by silica column chromatography (acetone:methylene chloride=1:4) to give 40 mg of a yellow foam solid compound (yield: 59%).

$^1$H-NMR (300 MHz, CDCl$_3$): δ=1.61-1.67 (m, 1H), 2.07-2.16 (m, 1H), 2.33-2.54 (m, 2H), 2.66-2.70 (m, 2H), 3.71 (s, 3H), 3.92 (s, 3H), 3.97 (s, 3H), 3.98 (s, 3H), 4.40-4.45 (t, 1H), 4.65-4.73 (m, 1H), 5.84-5.87 (d, 1H, J=6.9 Hz), 6.54 (s, 1H), 6.79-6.83 (d, 1H, J=10.6 Hz), 7.23-7.46 (m, 8H), 7.74-7.76 (m, 2H);

MS (m/e, M+): 563

EXAMPLE 24

Preparation of 3-(9H-fluoren-9-yl)-N-(1,2,3,10-tetramethoxy-9-oxo-5,6,7,9-tetrahydro-benzo[a]heptalen-7-yl)-propionamide (Compound 24)

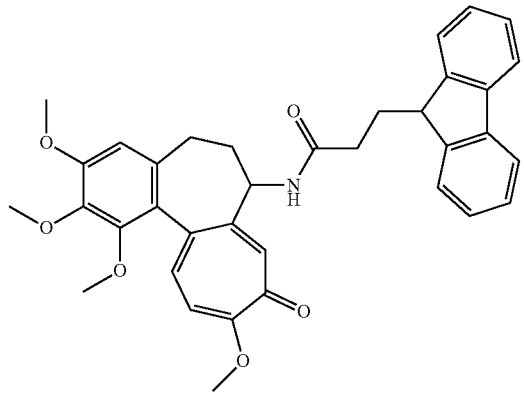 [SMILES: COc1cc2c(c(OC)c1OC)-c1ccc(OC)c(=O)cc1C(NC(=O)CCC1c3ccccc3-c3ccccc31)CC2]

100 mg (0.28 mmol) of the compound obtained in Preparation Example <1-3> was dissolved in 3 mL of methylene chloride, and then 80 mg (0.42 mmol) of 1-[3-(dimethylamino) propyl]-3-ethylcarbodiimide (EDC), 18 mg (0.14 mmol) of 1-hydroxybenzotriazole (HOBt), 116 μl (0.84 mmol) of triethylamine, and 100 mg (0.42 mmol) of the compound obtained in Preparation Example <2-6> were added at 0° C. and stirred at room temperature for 24 hours. The solvent was removed under reduced pressure, the residue was dissolved again in 50 mL of methylene chloride, and then the organic layer was washed with distilled water three times. The organic layer was dried with anhydrous sodium sulfate and filtered, and the residue obtained by concentrating the filtrate under reduced pressure was purified by silica column chromatography (acetone:methylene chloride=1:4) to give 110 mg of a yellow foam solid compound (yield: 68%).

$^1$H-NMR (300 MHz, CDCl$_3$) δ 1.58-1.88 (m, 3H), 2.00-2.12 (m, 1H), 2.27-2.48 (m, 4H), 3.65 (s, 3H), 3.89 (s, 3H), 3.94 (s, 3H), 3.95 (s, 3H), 4.04-4.06 (t, 1H), 4.42-4.50 (m, 1H), 6.00-6.02 (d, 1H, J=6.7 Hz), 6.50 (s, 1H), 6.77-6.80 (d, 1H, J=10.8 Hz), 7.18-7.37 (m, 6H), 7.42-7.48 (m, 2H), 7.70-7.73 (d, 2H, J=7.3 Hz)

MS (m/e, M+): 577

EXAMPLE 25

Preparation of 1-benzyl-3-(1,2,3,10-tetramethoxy-9-oxo-5,6,7,9-tetrahydro-benzo[a]heptalen-7-yl)-urea (Compound 25)

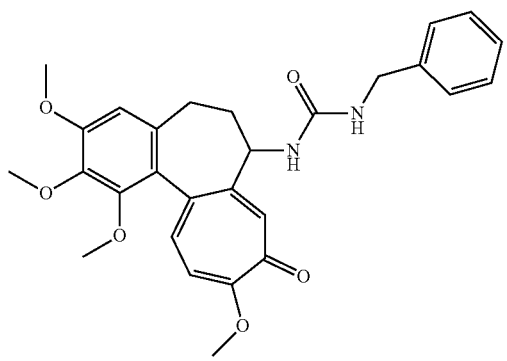 [SMILES: COc1cc2c(c(OC)c1OC)-c1ccc(OC)c(=O)cc1C(NC(=O)NCc1ccccc1)CC2]

100 mg (0.28 mmol) of the compound obtained in Preparation Example <1-3> and 38 μl (0.31 mmol) of benzylisocyanate were dissolved in 2 mL of methylene chloride and then reacted at room temperature for 1 hour. After the reaction was quenched, the reaction solution was concentrated and purified by column chromatography (5% methanol/dichloromethane) to give 125 mg of a white solid (yield: 91%).

$^1$H-NMR (300 MHz, CDCl$_3$) δ 1.87 (m, 1H), 2.52 (m, 3H), 3.67 (s, 3H), 3.70 (s, 3H), 3.92 (s, 3H), 3.95 (s, 3H), 4.23 (dd, J=6.0 Hz, 15.0 Hz, 1H), 4.41 (dd, J=6.0 Hz, 15.0 Hz, 1H), 4.81 (m, 1H), 6.11 (m, 1H), 6.55 (s, 1H), 6.75 (d, J=10.5 Hz, 1H), 6.84 (m, 1H), 7.11 (m, 1H), 7.19 (m, 3H), 7.35 (d, J=10.5 Hz, 1H), 7.96 (s, 1H)

MS (m/e, M): 490

EXPERIMENTAL EXAMPLES

The following experiments were performed on the compound of formula 1 according to the present invention to investigate various pharmacological actions. The dose of the colchicine derivatives depends on and varies with the age, weight, expected therapeutic effect, administration route, treatment period, etc. of an animal or human. However, satisfactory effects can be obtained using doses of 10, 50, 100 to 500 μg/kg.

Experimental Example 1

Cytotoxicity Test

Cytotoxicity test was performed to determine the toxicity of immunosuppressant candidate materials by mixing the immunosuppressant candidate materials with spleen cells of rats in culture media and measuring the degree of toxicity in the cells. In detail, rat spleen cells were seeded at a cell density of 5×10$^5$ cells per well in a 96-well plate, and cyclosporin A and the colchicine derivatives of the present invention were added thereto. The concentrations of the drugs were 0.1, 1, 10, 100, 1000, 10000, and 100000 ng/mL. The cells were cultured in a $CO_2$ incubator for 72 hours, and then each well was treated with 10 μl of CCK-SK (Dojindo, Japan). Subsequently, the cells were cultured again in the $CO_2$ incubator for 4 hours, and then the absorbance (O.D. value) was measured at 450 nm using a spectrophotometer.

As a result of the experiment, it was found that the colchicine derivative compounds of the present invention (compounds 1, 7, 9, 14, 15, 17, 18, 22, and 23) had no cytotoxicity even at concentrations of 100 ng to 10000 ng/mL.

Experimental Example 2

Measurement of Immunosuppressive Functions Using Mixed Lymphocyte Reaction (MLR) Test Mixed lymphocyte reaction (MLR) test was performed to examine immunomodulatory effects of the colchicine derivatives according to the present invention. When both responder cells (Wistar rat spleen cells) and stimulator cells (Lewis rat spleen cells, irradiated) are cultured alone, the growth of cells often does not occur. However, when both cells are co-cultured, the cells proliferate by cell-cell interaction. Here, it is possible to determine the immunomodulatory effects of immunomodulator candidate materials by mixing the immunomodulator candidate materials with the proliferating cells and measuring the degree of proliferation inhibition.

In detail, responder cells (Wistar rat spleen cells, $2.5 \times 10^5$ cells per well) and stimulator cells (Lewis rat spleen cells, $5 \times 10^5$ cells per well) were co-cultured and treated with the colchicine derivatives of the present invention. Cyclosporin A was used as a control group. The concentrations of the drugs were 0.1, 1, 10, 100, 1000, 10000, and 100000 ng/mL. The cells were cultured in a $CO_2$ incubator for 72 hours. On day 2 all wells were pulsed with $^3$H-thymidine and incubated for a further 24 h at 37° C. under 5% $CO_2$. After cell harvest, thymidine incorporation was measured using a β-counter As a result of the measurement, as shown in FIG. 1a and FIG. 1b, it was found that the colchicine derivative compounds of the present invention (compounds 1, 7, 9, 14, 15, 17, 18, 22, and 23) inhibited the growth of the cells at concentrations of 100 to 1000 ng/mL, indicating that the compounds of the present invention had superior immunomodulatory effects.

Experimental Example 3

Modulation of Immune Response According to Allogeneic Heart Transplantation

Hearts of 8-week-old Lewis rats (donor) weighing about 250 g were extracted and performed abdominal heterotopic heart transplantation into the abdominal cavity of 8-week-old Wistar rat (recipient) weight about 300 g by cross-clamping caudal vena cava and the abdominal aorta of recipient both proximally and distally to the anastomotic site. After the heart transplantation, cyclosporin A (5 mg/kg), colchicine (10 μg and 40 μg/kg), and colchicine derivative compound 14 (10 μg and 40 μg/kg) were intravenously injected to experimental groups, respectively, for 14 days.

The heart rate of each rat in an untreated control group and the experimental groups was measured by abdominal palpation from the date of the heart transplant, and the heart rate was classified as ++++ (strong and fast heartbeat), +++ (strong or fast heartbeat), ++ (faint and slow but distinct heartbeat), + (faint but steady heartbeat), and ±0 (intermittent heartbeat). The measurement results are shown in the following table 2.

TABLE 2

Allogeneic heart transplantation

| Group | | Population | Number of days for which heart rate was kept (day) | Average (day) |
|---|---|---|---|---|
| Control group | | 8 | 7, 7, 8, 9, 9, 11, 11, 12 | 9.2 ± 1.9 |
| CsA (5 mg/kg) | | 3 | 166, >182, >200 | 182.6 ± 17.0 |
| Colchicine | 10 μg/kg | 3 | 12, 12, >186 | >70 ± 100.5 |
| | 40 μg/kg | 4 | 13, 14, >32*, >187 | >73.3 ± 85.4 |
| Compound 14 | 10 μg/kg | 3 | 9, >139, >173 | >107 ± 86.6 |
| | 40 μg/kg | 2 | >173, >174 | >173.5 ± 0.7 |

*Death

As a result of the experiment, it could be seen that the heartbeat was stopped due to rejection of transplanted hearts in the untreated control group after 8 to 9 days.

On the contrary, it was observed that in the experimental group, to which cyclosporin A (5 mg/kg) was administered, the heartbeat of one rat was stopped after 166 days, and the heartbeat of two rats continued over 200 days and 182 days. Moreover, it was observed that in the experimental group, to which colchicine (10 μg/kg) was administered, the heartbeat of two rat was stopped after 12 days, and the heartbeat of one rat continued over 186 days, and in the experimental group, to which colchicine (40 μg/kg) was administered, the heartbeat of two rat was stopped after 13 days and 14 days, and the heartbeat of one rat continued over 187 days.

Meanwhile, it was observed that in the experimental group, to which colchicine derivative compound 14 (10 μg/kg) was administered, the heartbeat of one rat was stopped after 9 days, and the heartbeat of two rats continued over 139 days and 173 days, and in the experimental group, to which colchicine derivative compound 14 (40 μg/kg) was administered, the heartbeat of all rats continued over 173 days and 174 days.

The above observations indicate that the colchicine derivatives of the present invention exhibit similar immunomodulatory effects even at a small amount compared to the cyclosporin A, and exhibit superior immunosuppressive effects, in particular, compared to the colchicines.

Experimental Example 4

Modulation of Immune Response According to Allogeneic Pancreatic Islet Cell Transplantation Streptozotocin is a drug that destroys pancreatic islet cells to induce diabetes and is used to create experimental diabetic animal models. Allogeneic islets were transplanted into the livers of streptozotocin induced diabetic rat by injection into the portal vein. The functioning of transplanted islets was assessed by daily measurements of blood glucose levels. Islets were considered rejected when the blood glucose level was 200 mg/dl on two consecutive days. Here, immunomodulators such as cyclosporin A, which are drugs to suppress the immune response, are used to prevent the transplanted islet cells from being destroyed.

35 mg/kg of streptozotocin (50 mg/mL) dissolved in a 0.1 M citrate buffer solution (pH 4.5) was intraperitoneally injected into 8-week-old male Fischer 344 rats (F344) weighing about 200 to 220 g. Then, the blood glucose level was measured after 1 week, and the first day when the blood glucose level increased over 300 mg/dl and the increase was repeated more than twice was considered as the date of diagnosis of diabetes. The rats were used in transplantation 3 weeks after the administration of streptozotocin.

Pancreases of 8-week-old male Lewis rats were extracted on the 3 weeks after the diabetes was induced in Fischer rats, and islet cells were isolated. The isolated islet cells were cultured in a $CO_2$ incubator at 37° C. for a day, and the cultured islet cells were transplanted into the diabetic Fischer rats.

<4-1> Single Intraperitoneal Administration

Cyclosporin (5 mg/kg), colchicine (10 μg/kg and 40 μg/kg), and colchicine derivative compounds (compounds 1, 7, 9, 14, 15, 17, 18, 22, and 23; 50 μg/kg) were administered to the Fischer rats, to which the islet cells were transplanted, for 14 days from the date of transplantation, and the maintenance of blood glucose levels was examined until rejection occurred from the date of transplantation. The experimental results are shown in the following table 3.

TABLE 3

Allogeneic pancreatic islet cell transplantation - Single intraperitoneal administration

| Group | | Population | Number of days for which islet cell function was maintained (day) | Average (day) |
|---|---|---|---|---|
| Control group | | 9 | 4, 5, 5, 5, 5, 5, 5, 5, 6 | 5 ± 0.5 |
| CsA (5 mg/kg) | | 5 | 5, 7, 7, 13, 14 | 9.2 ± 4.02 |
| Colchicine | 10 μg/kg | 2 | 5, 5 | 5 |
| | 40 μg/kg | 4 | 2*, 2*, 6, 9* | 6 |
| Compound 7 | 50 μg/kg | 3 | 5, 5, 7 | 5.7 ± 1.16 |
| Compound 9 | 50 μg/kg | 3 | 5, 6, 6 | 5.7 ± 0.58 |
| Compound 14 | 10 μg/kg | 2 | 5, 5 | 5.5 ± 0.71 |
| | 40 μg/kg | 2 | 6, 7 | 6.5 ± 0.71 |

*Death

As a result of the experiment, it could be seen that rejection of the transplanted islet cells occurred in the untreated control group after 5 to 6 days. On the contrary, the rejection of the transplanted islet cells was observed after an average of 9 days in the experimental group to which cyclosporin (5 μg/kg) was administered alone. Moreover, the rejection of the transplanted islet cells was observed after days in the experimental group to which colchicine (10 μg/kg) was administered alone. It could be seen that in the experimental group to which colchicines (40 μg/kg) was administered alone, two of the four rats were dead with a 15% weight reduction on the second day, one rat was dead suddenly after 9 days, while maintaining the blood glucose level, and the rejection of the transplanted islet cells occurred in the remaining one rat after 6 days.

Meanwhile, it could be seen that the rejection of the transplanted islet cells occurred after 5 days to 7 days in the experimental group to which colchicine derivative compound 7 (50 μg/kg) was administered alone, after 5 days to days in the experimental group to which colchicine derivative compound 9 (50 μg/kg) was administered alone, after 5 days to 6 days in the experimental group to which colchicine derivative compound 14 (10 μg/kg) was administered alone, and after 6 days to 7 days in the experimental group to which colchicine derivative compound 14 (40 μg/kg) was administered alone.

In the single administration, the cyclosporin A maintained blood glucose levels more than 4 days, compared to the untreated control group, and the colchicine and the colchicine derivatives showed no significant differences from the control group. This indicates that the islet cells have strong immune response, and thus the cyclosporin A, the colchicine, or the derivative thereof does not exhibit significant effects.

<4-2> Combined Intraperitoneal Administration

Since there were no effects in the single administration, the cyclosporin A (5 mg/kg) and the colchicine derivative compounds were administered together for 14 days from the date of islet cell transplantation, and the maintenance of blood glucose levels was examined. However, considering the interaction between the two drugs, the two drugs were introduced in different syringes and injected to right and left sides of the abdominal cavity, respectively, and the measurement results are shown in the following table 4.

TABLE 4

Allogeneic pancreatic islet cell transplantation - Combined intraperitoneal administration

| Group | Population | Number of days for which islet cell function was maintained (day) | Average (day) |
|---|---|---|---|
| CsA (5 mg/kg) + Colchicine (10 μg/kg) | 3 | 5, 6, 13 | 8 ± 4.36 |
| CsA (5 mg/kg) + Compound 1 (50 μg/kg) | 2 | 27, 27 | 27 |
| CsA (5 mg/kg) + Compound 7 (50 μg/kg) | 5 | 14, 15, 24, >101, >154 | >61.6 ± 63.13 |
| CsA (5 mg/kg) + Compound 7 (100 μg/kg) | 3 | 33, >70, >113 | >72 ± 40.04 |
| CsA (5 mg/kg) + Compound 9 (50 μg/kg) | 3 | 27, 32, >108 | >55.7 ± 45.4 |
| CsA (5 mg/kg) + Compound 14 (10 μg/kg) | 3 | 27, 29, 30 | 28.7 ± 1.53 |
| CsA (5 mg/kg) + Compound 14 (40 μg/kg) | 9 | 24, 25, 27, 28, 33, 47, 70, >101, >201 | >61.8 ± 58.3 |
| CsA (5 mg/kg) + Compound 15 (50 μg/kg) | 2 | 24, 24 | 24 |
| CsA (5 mg/kg) + Compound 17 (50 μg/kg) | 4 | 23, 24, 26, 74 | 36.5 ± 24.9 |
| CsA (5 mg/kg) + Compound 18 (50 μg/kg) | 2 | 27, 29 | 28 ± 1.41 |
| CsA (5 mg/kg) + Compound 22 (50 μg/kg) | 3 | 5, 6, 51 | 20.7 ± 26.3 |
| CsA (5 mg/kg) + Compound 23 (50 μg/kg) | 2 | 22, 31 | 26.5 ± 6.36 |

As a result of the experiment, it was found that the number of days for which the islet cell function was maintained was an average of 8 days in the experimental group to which the colchicine (10 μg/kg) was administered in combination with the cyclosporin A (5 mg/kg), which was increased by about 3 days, compared to the single administration. On the contrary, it could be seen that the experimental groups to which the colchicine derivative compounds were administered in combination with the cyclosporin A (5 mg/kg) maintained the islet cell function longer and thus exhibited superior immunomodulatory effects, compared to the single administration, and compared to the combined administration of cholchicine (10 ug/kg) and cyclosporin A (5 mg/kg)).

In particular, during the combined administration of the cyclosporin A and the colchicine derivatives of the present invention, the islet cell function lasted for an average of 20 days or longer. Moreover, in the case of compounds 7, 9, and 14, the immunomodulatory effects lasting for more than 100 days show that the combined administration is more advantageous than the single administration in the case of the islet cell transplantation. Furthermore, the fact that the effects on the regulation of blood glucose were high even with the short-term administration demonstrates that the colchicine derivatives of the present invention exhibit superior immunomodulatory effects compared to the colchicines.

<4-3> Continuous Combined Intraperitoneal Administration

To verify the immunomodulatory effects during continuous combined intraperitoneal administration, after the cyclosporin A (5 mg/kg) and compound 14 (40 to 500 μg/kg)

were injected for 14 days (2 weeks) from the date of islet cell transplantation, single or combined administration was continuously performed under the conditions shown in the following table 5, and the maintenance of blood glucose levels was examined. However, considering the toxicity of cyclosporin, the amount of cyclosporin A was reduced from 5 mg/kg to 2 mg/kg after 30 days. The measurement results are shown in the following table 5.

TABLE 5

Allogeneic pancreatic islet cell transplantation - Continuous combined intraperitoneal administration

| Group | Population | Number of days for which islet cell function was maintained (day) | Average (day) |
| --- | --- | --- | --- |
| CsA (5 mg/kg) & Compound 14 (500 μg/kg) were injected for 2 weeks | 3 | 25, 30, 32 | 29 ± 3.61 |
| After CsA (5 mg/kg) & Compound 14 (500 μg/kg) were injected for 2 weeks, only CsA (5 mg/kg) was injected | 2 | 40, 57 | 48.5 ± 12.0 |
| After CsA (5 mg/kg) & Compound 14 (500 μg/kg) were injected for 2 weeks, only compound 14 (500 μg/kg) was injected | 3 | 20, 25, 113 | 52.7 ± 52.3 |
| After CsA (5 mg/kg) & Compound 14 (40 μg/kg) were injected for 2 weeks, CsA (5 mg/kg) & compound 14 (40 μg/kg) were continuously injected | 2 | 56, >70 | >63 ± 9.9 |
| After CsA (5 mg/kg) & Compound 14 (500 μg/kg) were injected for 2 weeks, CsA (5 mg/kg) & compound 14 (500 μg/kg) were continuously injected | 3 | 40, 81, 82 | 67.7 ± 24.0 |

As shown in the above table 5, in the experimental group to which the cyclosporin A or compound 14 was administered alone after the combined administration for 2 weeks, the islet cell function was maintained about 1.6 to 1.8 times compared to the experimental group to which the cyclosporin A and compound 14 are administered for 2 weeks only. Moreover, the experimental groups to which the two drugs are continuously administered together even after the combined administration for 2 weeks, the islet cell function was improved about 2.3 times compared to the experimental group to which the cyclosporin A and compound 14 are administered for 2 weeks only, and about 1.28 to 1.3 times compared to the experimental group to which cyclosporin A or compound 14 was administered alone after the combined administration for 2 weeks.

The above results indicate that the combined administration of the cyclosporin A and the colchicine derivatives of the present invention after the islet cell transplantation is more effective in maintaining the functions of the transplanted islet cells and the colchicine derivatives of the present invention have no side effects even with the long-term administration.

Experimental Example 5

Analysis of Transplanted Organ Tissues

Insulin staining was performed on liver tissues and pancreatic tissues to determine whether islet cells transplanted into liver tissues are infused and secrete insulin or whether the islet cells are regenerated in the pancreas and secrete insulin, and hematoxylin and eosin (H&E) staining was performed to determine changes in the tissues. At the same time, CD4 and CD8 staining was performed to determine T cell infiltration.

Tissues used in the staining were those extracted from the liver and pancreas of the rats, whose islet cell function was maintained over 100 days, among the experimental groups to which the cyclosporin A and the colchicine derivative compounds (7, 9 and 14) were administered under the conditions shown in table 4 after the islet cell transplantation, and kept in 10% formalin.

First, for insulin staining, the tissues were embedded in paraffin and cut into slices of 2 to 3 μm in thickness. Each slice was kept at 60° C. for 30 minutes such that the tissue was not separated from the slide during the staining, and then the paraffin was removed with xylene. Subsequently, each slide was sequentially treated with 100%, 95%, and 90% alcohols, treated with normal horse serum (Vectastain kit, Vector, USA), and stained with anti-insulin antibody (primary antibody: Dako, USA) for 1 hour. Then, the resulting slide was stained with secondary antibody (Vectastain kit, Vector, USA) for 30 minutes, stained with DAB for 2 minutes, counterstained with hematoxylin for 1 minute, washed for any excess stain, and then dried. The dried slide was dipped in xylene and mounted in Permount, and then the presence of insulin staining was examined under an optical microscope.

The CD4 and CD8 staining was performed in the same manner as the insulin staining.

Meanwhile, for hematoxylin and eosin staining, the tissues were embedded in paraffin and cut into slices of 2 to μm in thickness. Each slice was kept at 60° C. for 30 minutes such that the tissue was not separated from the slide during the staining, and then the paraffin was removed with xylene. Subsequently, each slide was sequentially treated with 100%, 95%, and 90% alcohols, and then nuclear staining was performed with Harris hematoxylin for 5 minutes. With respect to the nuclear-stained slides, the excess stain was decolorized with an acidic alcohol solution, dyed with mordant using an ammonia solution, and then cytoplasmic staining was performed with eosin. Then, the resulting slide was sequentially treated with 90%, 95%, and 100% alcohols, dehydrated, substituted with xylene, and mounted in Permount, and then the changes in liver tissues of the transplanted islet cells were examined under an optical microscope.

The experimental results are shown in FIG. 2. As shown in FIG. 2, it was found from the analysis of liver and pancreas tissues of the rats, whose islet cell function was maintained over 100 days, and to which the cyclosporin A and the colchicine derivative compounds were administered together after the islet cell transplantation, that the islet cells infused into liver tissues were viable by the positive insulin staining, while islet cells were destroyed in the pancreas by negative insulin staining. It could be seen from the experimental results of the hematoxylin and eosin staining that when the pancreatic islet cell function was maintained over 100 days, the liver tissues were kept very clear, and there were fewer immune cells infiltrating into the tissues. It could be confirmed from the experimental results of the CD4 and CD8 staining that there were very few immune cells infiltrating into the tissues.

The above-described compounds of the present invention may be formulated into various forms. While various formulations containing the compound of the present invention were prepared based on the following preparation examples, the present invention is not limited thereto.

Preparation Example 1

Tablets (Direct Compression)

5.0 mg of active ingredient was sieved, mixed with 14.1 mg of lactose, 0.8 mg of CrossPovidone USNF, and 0.1 mg of magnesium stearate, and then compressed to form tablets.

Preparation Example 2

Tablets (Wet Granulation)

5.0 mg of active ingredient was sieved and mixed with 16.0 mg of lactose and 4.0 mg of starch. 0.3 mg of Polysorbate 80 was dissolved in purified water, and an appropriate amount of this solution was added to the mixture and granulated. The granules were sieved and mixed with 2.7 mg of colloidal silicon dioxide and 2.0 mg of magnesium stearate and then compressed to form tablets.

Preparation Example 3

Powders and Capsules 5.0 mg of active ingredient was sieved and mixed with 14.8 mg of lactose, 10.0 mg of polyvinyl pyrrolidone, and 0.2 mg of magnesium stearate. The mixture was filled in a hard No. 5 gelatin capsule using an appropriate apparatus.

Preparation Example 4

Injections 100 mg of active ingredient, 180 mg of mannitol, 26 mg of $Na_2HPO_4 \cdot 12H_2O$, and 2974 mg of distilled water were mixed to form injections.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

The invention claimed is:

1. The colchicine derivative or the pharmaceutically acceptable salt thereof, the derivative being selected from the group consisting of:
   (1,2,3,10-tetramethoxy-9-oxo-5,6,7,9-tetrahydro-benzo[a]heptalen-7-yl)-carbamic acid benzyl ester;
   (1,2,3,10-tetramethoxy-9-oxo-5,6,7,9-tetrahydro-benzo[a]heptalen-7-yl)-carbamic acid 4-methoxy benzyl ester;
   (1,2,3,10-tetramethoxy-9-oxo-5,6,7,9-tetrahydro-benzo[a]heptalen-7-yl)-carbamic acid 4-isopropyl benzyl ester;
   (1,2,3,10-tetramethoxy-9-oxo-5,6,7,9-tetrahydro-benzo[a]heptalen-7-yl)-carbamic acid 9H-fluoren-9-ylmethyl ester;
   (1,2,3,10-tetramethoxy-9-oxo-5,6,7,9-tetrahydro-benzo[a]heptalen-7-yl)-carbamic acid 1-methyl-9H-fluoren-9-ylmethyl ester;
   (1,2,3,10-tetramethoxy-9-oxo-5,6,7,9-tetrahydro-benzo[a]heptalen-7-yl)-carbamic acid 2,7-di-tert-butyl-9H-fluoren-9-ylmethyl ester; and
   (1,2,3,10-tetramethoxy-9-oxo-5,6,7,9-tetrahydro-benzo[a]heptalen-7-yl)-carbamic acid 2-(9H-fluoren-9-yl)-ethyl ester.

2. A method for preparing a colchicine derivative of claim 1, the method comprising the step of reacting a deacetyl colchicine derivative represented by the following formula 2 with an equivalent amount or an excess of

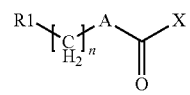

in the presence of a base or a condensing agent in a reaction solvent to form amide;

[Formula 2]

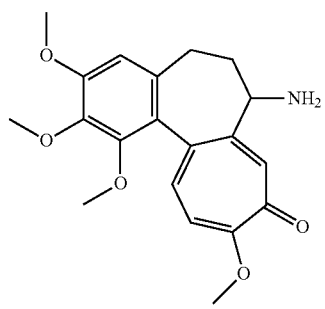

wherein R1 is one of the following:

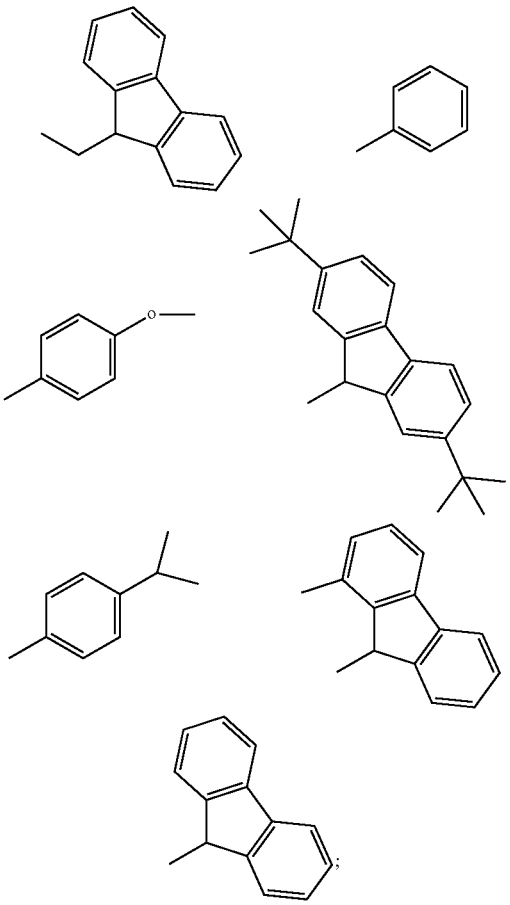

X is halogen;
n is 1; and
A is O.

3. The pharmaceutical composition for immunomodulation, the pharmaceutical composition comprising the colchicine derivative or the pharmaceutically acceptable salt thereof of claim 1 and further comprising an immunosuppressant.

4. The pharmaceutical composition for immunomodulation of claim 3, wherein the immunosuppressant is selected from the group consisting of cyclosporin A, tacrolimus, prednisolone, deflazacort, mycophenolic acid, azathioprine, mizoribine, sirolimus, everolimus, anti-CD25 antibody, anti-CD3 antibody (OKT3), anti-CD20 antibody, and combinations thereof.

5. The pharmaceutical composition for immunomodulation of claim 1, wherein the pharmaceutical composition modulated an acute or chronic immune response in organ transplantation.

6. A method for inhibiting an immune response in organ transplant, the method comprising administering the colchicine derivative or the pharmaceutically acceptable salt thereof of claim 1 to a subject requiring the same.

7. The method of claim 6, wherein the colchicine derivative or the pharmaceutically acceptable salt thereof is administered in combination with other immunomodulators.

\* \* \* \* \*